United States Patent
Akagane

(10) Patent No.: US 12,108,977 B2
(45) Date of Patent: Oct. 8, 2024

(54) TREATMENT INSTRUMENT

(71) Applicant: OLYMPUS MEDICAL SYSTEMS CORP., Tokyo (JP)

(72) Inventor: Tsunetaka Akagane, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 141 days.

(21) Appl. No.: 17/881,932

(22) Filed: Aug. 5, 2022

(65) Prior Publication Data

US 2023/0046955 A1 Feb. 16, 2023

Related U.S. Application Data

(60) Provisional application No. 63/232,404, filed on Aug. 12, 2021.

(51) Int. Cl.
*A61B 18/14* (2006.01)
*A61B 17/32* (2006.01)
*A61B 18/00* (2006.01)

(52) U.S. Cl.
CPC .. *A61B 18/1445* (2013.01); *A61B 17/320092* (2013.01); *A61B 2018/00607* (2013.01); *A61B 2018/00994* (2013.01)

(58) Field of Classification Search
CPC ........ A61B 18/1445; A61B 17/320092; A61B 2018/00607; A61B 2018/00994; A61B 18/085; A61B 2017/00876; A61B 2018/00202; A61B 2018/00589; A61B 2018/0063; A61B 2018/0091; A61B 2030/035

See application file for complete search history.

(56) References Cited

U.S. PATENT DOCUMENTS

| 5,269,797 | A | * | 12/1993 | Bonati ............... A61B 17/3417 606/174 |
| 9,456,863 | B2 | | 10/2016 | Moua |
| 2018/0271550 | A1 | * | 9/2018 | Rodriguez-Navarro ..................... A61B 17/1285 |

* cited by examiner

*Primary Examiner* — Keith M Raymond
*Assistant Examiner* — Partick M Mehl
(74) *Attorney, Agent, or Firm* — Morgan, Lewis & Bockius LLP

(57) ABSTRACT

Treatment instrument with movable handle and fixed handle includes biasing member for biasing the movable handle in an opening direction and an assist system with attraction force, e.g., magnetic force, to attract the movable handle in a closing direction toward the fixed handle. Range of movement of movable handle includes first movable range and second movable range. The second movable range occurs when a second gripping piece, e.g. a jaw, is in contact with respect to a first gripping piece, e.g., a vibration transmission member, and the movable handle is then further moved in a direction toward the fixed handle to a fully closed position. In the second movable range, attraction forces associated with the assist system are smaller than biasing force from the biasing member so that, upon release of a gripping force by an operator, the movable handle moves away from the fixed handle.

20 Claims, 16 Drawing Sheets

TREATMENT INSTRUMENT

RELATED APPLICATION DATA

This application is based on and claims priority under 35 U.S.C. § 119 to U.S. Provisional Application No. 63/232,404 filed on Aug. 12, 2021, the entire contents of which are incorporated herein by reference.

FIELD OF THE DISCLOSURE

The present invention relates to a treatment instrument.

BACKGROUND

Conventionally, there has been known a treatment instrument which treats a site of interest by imparting treatment energy to a site (hereinafter, described as a target site) to be treated in a biological tissue (see, for example, Patent Document 1). The treatment instrument described in Patent Document 1 includes a first and a second gripping piece, which are openable and closable with respect to each other and which can grasp a target site, an opening/closing mechanism which opens/closes the first and second gripping pieces, and a movable handle which accepts a user operation by an operator. In response to the user operation of the movable handle, the opening and closing mechanism operate and the first and second gripping pieces are relatively opened and closed.

Prior art documents—Patent Document 1: U.S. Pat. No. 9,456,863.

SUMMARY OF THE INVENTION

Problem to be Solved by the Invention

In the treatment instrument described in Patent Document 1, a spring is mounted in order to provide a constant gripping force for grasping a target site between the first and second gripping pieces. When the spring acts, a reaction force is applied to the movable handle in response to a user operation on the movable handle. Therefore, in operating the movable handle, an operator such as a medical professional needs to apply a force against the reaction force, and a large amount of force is often required.

Therefore, it is desirable to improve the operability of a treatment instrument by reducing the force required in operating the movable handle.

In view of the above, it is an object of the present invention to provide a treatment instrument capable of improving operability.

Means for Solving the Problem

In order to solve the above problems and achieve the object, a treatment tool according to the present invention includes: a first grip piece; a second grip piece configured to be openable and closable with respect to the first grip piece and configured to grasp living tissue between the first grip piece; a shaft having the second grip piece connected to a distal end thereof; a fixed handle connected to a proximal end of the shaft; a movable handle moving in a direction toward or away from the fixed handle; a biasing member for biasing the movable handle in a direction away from the fixed handle when the movable handle moves in a direction proximate to the fixed handle; and an assist system for generating an attractive force by a magnetic force to attract the movable handle to the fixed handle by a user's manipulation of the movable handle; and the second grip piece moves proximate to the first grip piece by causing the movable handle to move in a direction proximate to the fixed handle. The movable handle moves in a direction away from the fixed handle in response to a user operation on the movable handle to separate the movable handle from the first grip piece, and the movable range of the movable handle has a first movable range from a state where the second grip piece is most separated from the first grip piece to a state where the second grip piece is in contact with the first grip piece in a state where nothing is gripped between the first grip piece and the second grip piece, and a second movable range from a state where the second grip piece is in contact with the first grip piece to a second movable range where the movable handle is movable in a direction where the movable handle is in contact with the fixed handle in response to a user operation on the movable handle, and the attractive force by the assist system is smaller than the urging force from the urging member to the handle in the second movable range.

Effect of the Invention

According to the treatment instrument according to the present invention, operability of the treatment instrument can be improved.

BRIEF DESCRIPTION OF THE DRAWING

The following detailed description of preferred embodiments can be read in connection with the accompanying drawings in which like numerals designate like elements and in which.

DETAILED DESCRIPTION

Modes for Carrying Out the Invention

Figure 1:
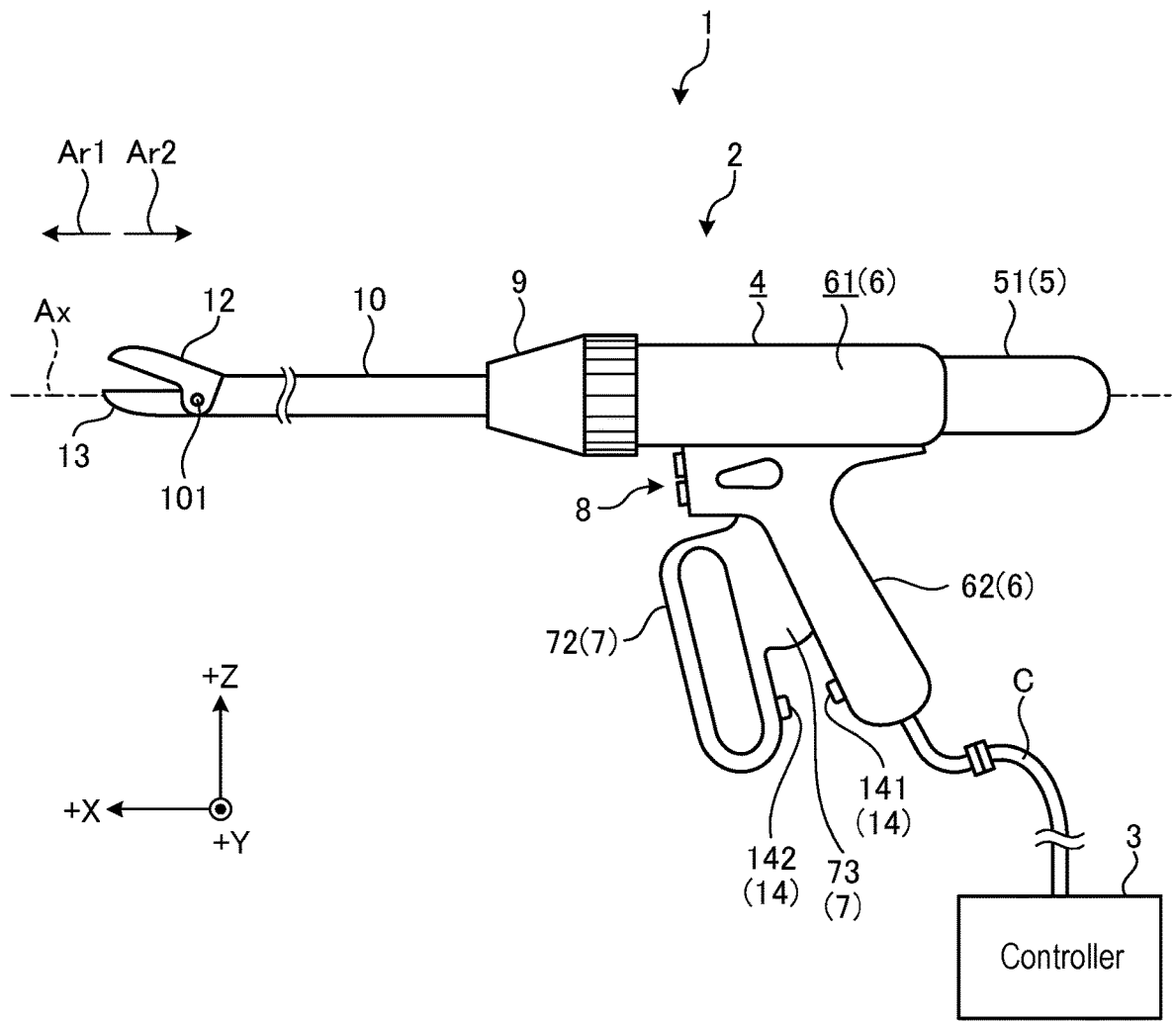
FIG. 1 is a diagram illustrating a treatment system according to the first embodiment.

Hereinafter, embodiments for carrying out the present invention (hereinafter, embodiments) will be described with reference to the accompanying drawings. Note that the present invention is not limited by the embodiments described below. In addition, in the description of the drawings, the same parts are denoted by the same reference numerals.

Embodiment 1

Schematic Configuration of the Treatment System

FIG. 1 is a diagram illustrating a treatment system 1 according to the first embodiment. The treatment system 1 treats the target site by imparting treatment energy to a site to be treated in a biological tissue (hereinafter, described as a target site). Note that the treatment energy in the first embodiment is ultrasonic energy and high frequency energy, but embodiments can include other treatment energies, such as heat energies and microwave energies. Further, a treatment operation that can be performed by the treatment system 1 according to the first embodiment is a treatment operation such as coagulation (sealing) of a target site or incision of a target site, but other treatment operations can be conducted with the treatment system, such as anastomosis. In addition, treatment operations, such as coagulation and incision, may be performed simultaneously. The treatment system 1 comprises a treatment instrument 2 and a controller 3, as shown in FIG. 1.

Structure of the Treatment Instrument

In the following, in describing the configuration of the treatment instrument 2, the X-axis, Y-axis, and Z-axis are mutually orthogonal, as shown by the XYZ coordinate axis in FIG. 1. The X-axis is an axis parallel to the central axis Ax of the shaft 10 (FIG. 1), the Y-axis is an axis perpendicular to the plane of the paper, and the Z-axis is an axis along the vertical direction of FIG. 1. In addition, in the following, one side along the central axis Ax (+X-axis side) is described as a distal end side Ar1, and the other side (−X-axis side) is described as a proximal end side Ar2.

Figure 2:
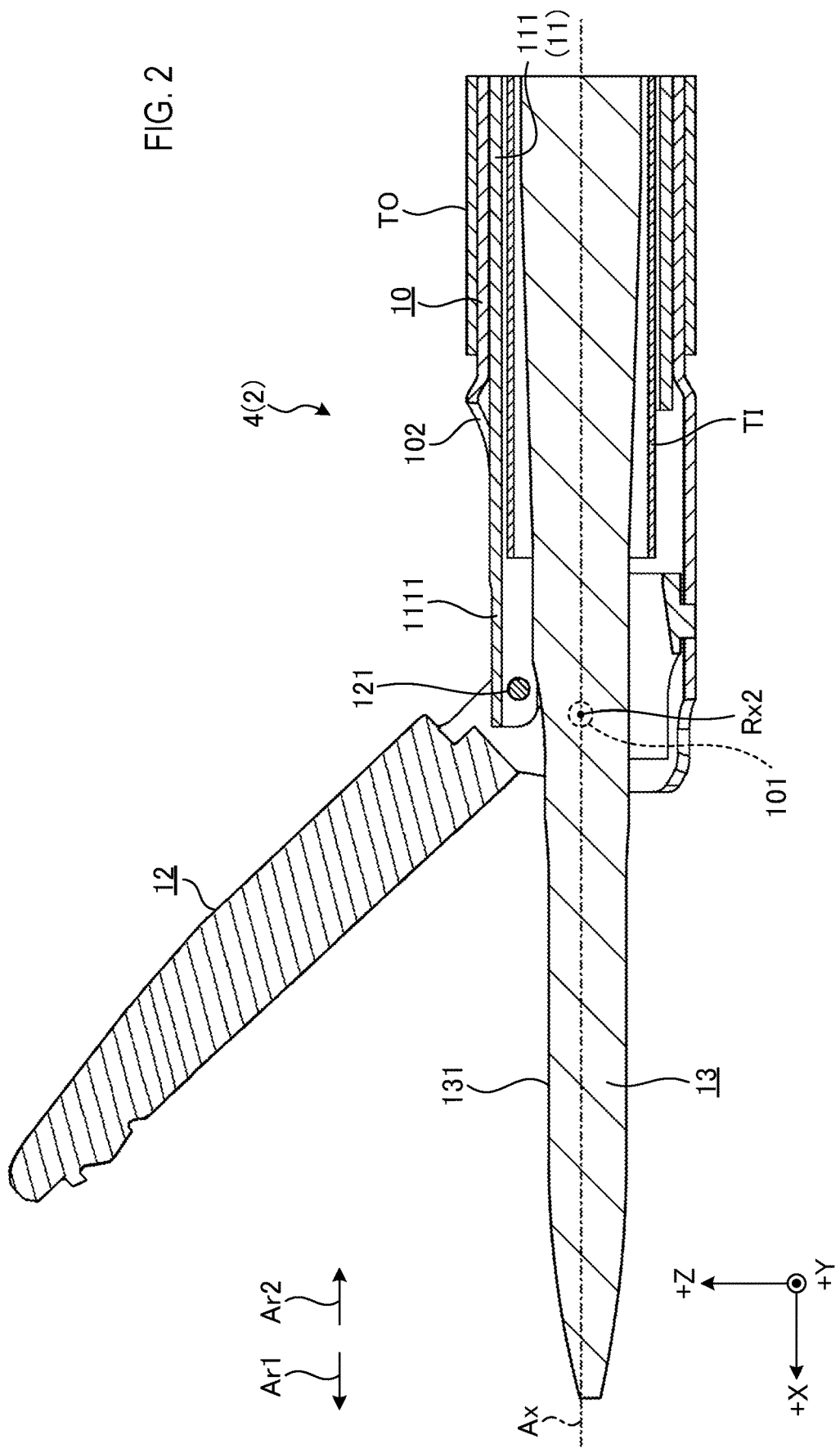
FIG. 2 is a diagram illustrating a configuration of a treatment instrument.
Figure 3:
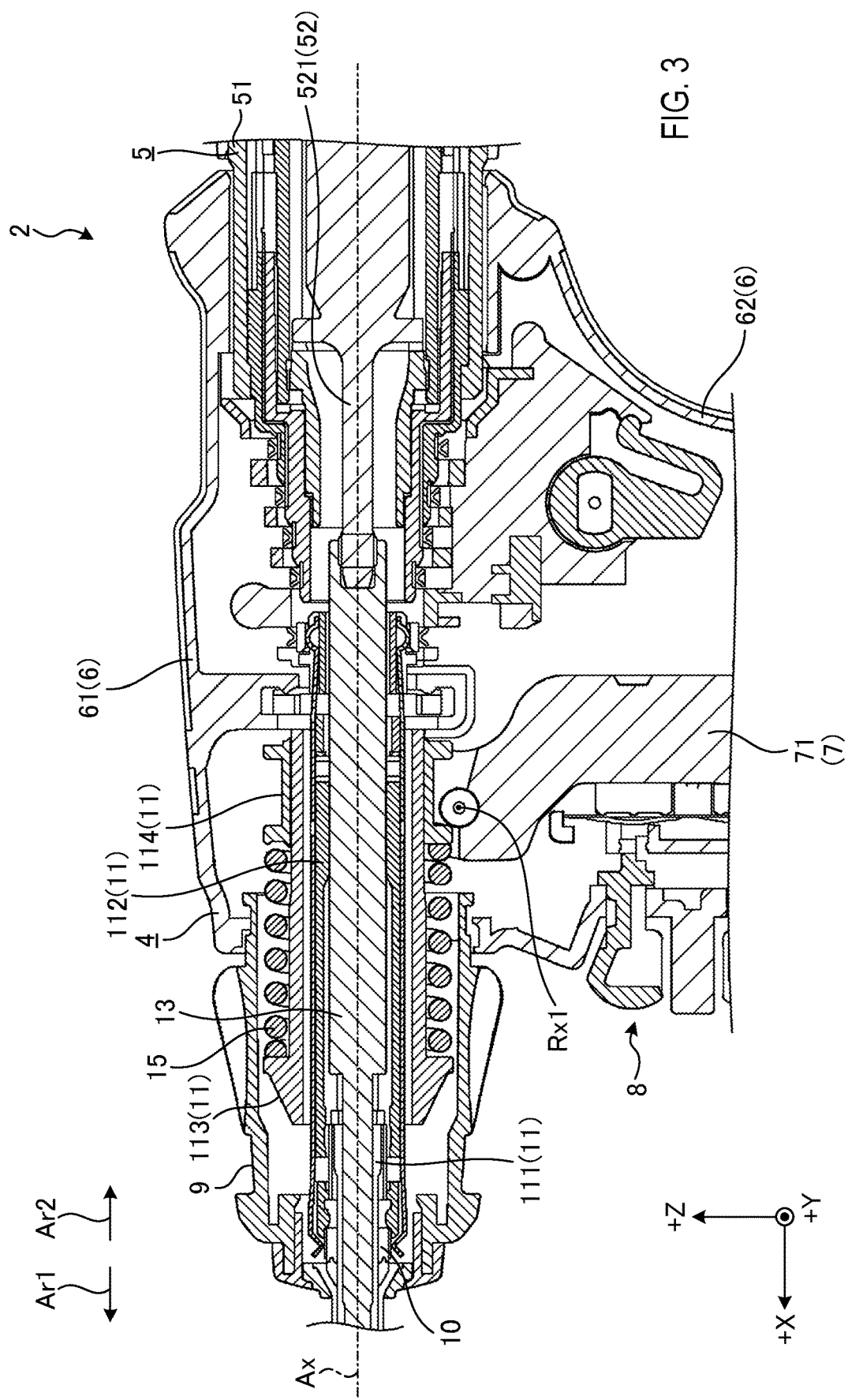
FIG. 3 is a diagram illustrating a configuration of a treatment instrument.
Figure 4:
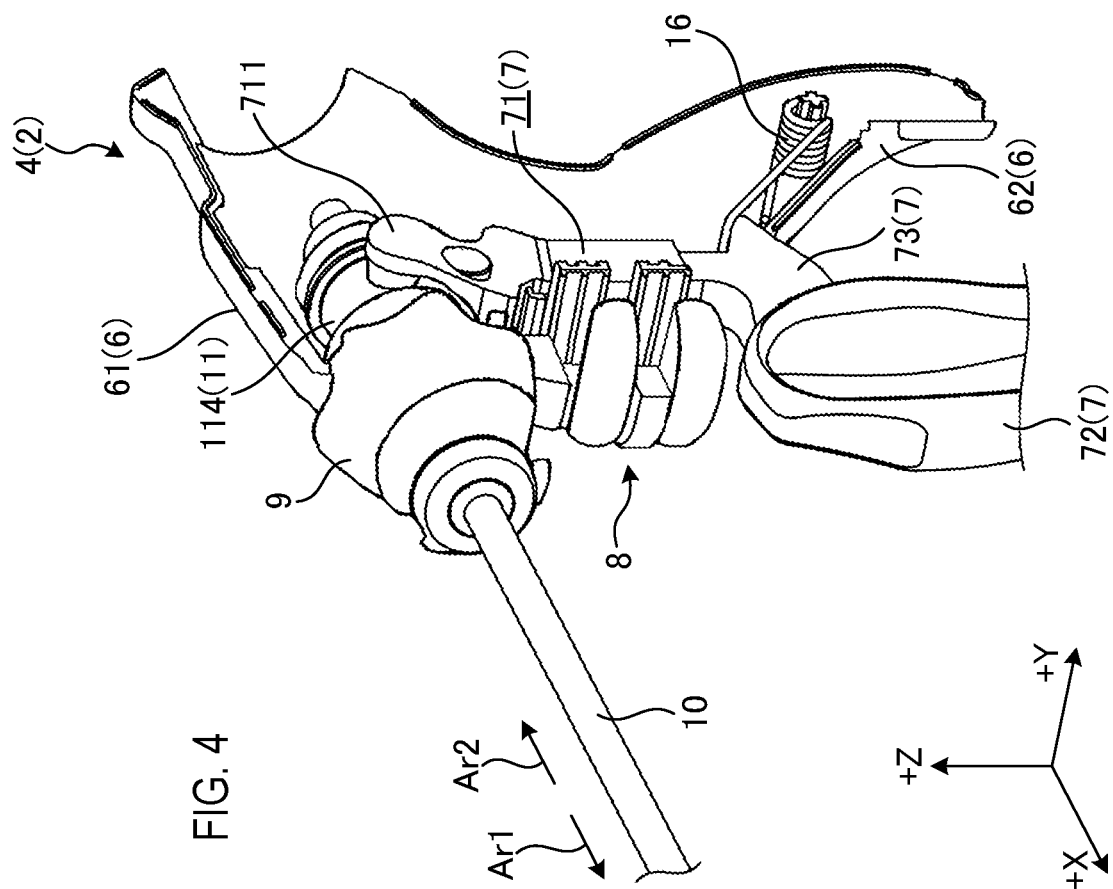
FIG. 4 is a diagram illustrating a configuration of a treatment instrument.

FIGS. 2 to 4 are views illustrating the configuration of the treatment instrument 2. Specifically, FIGS. 2 and 3 are cross-sectional views (as viewed from the +Y-axis side with cutting the treatment instrument 2) in the XZ plane including the central axis Ax. FIG. 4 is a view showing the interior of the fixed handle 6.

The treatment instrument 2 is an ultrasonic treatment instrument which treats the target site by imparting ultrasonic energy and high frequency energy to the target site. The treatment instrument 2 comprises a handpiece 4 and an ultrasonic transducer 5, as shown in FIGS. 1-4.

As shown in FIGS. 1 to 4, the handpiece 4 includes a fixed handle 6 (FIGS. 1, 3, and 4), a movable handle 7 (FIGS. 1, 3, and 4), a switch 8 (FIGS. 1, 3, and 4), a rotary knob 9 (FIGS. 1, 3, and 4), a shaft 10, an opening and closing mechanism 11 (FIGS. 2 to 4), a jaw 12 (FIGS. 1 and 2), a vibration transmission member 13 (FIGS. 1 to 3), an assist system 14 (FIG. 1), a first biasing member 15 (FIG. 3), and a second biasing member 16 (FIG. 4).

The fixed handle 6 supports the treatment instrument 2. As shown in FIGS. 1, 3, and 4, the fixed handle 6 includes a substantially cylindrical case body 61, which is coaxial with the central axis Ax, and a handle body 62, which extends from the case body 61 to the −Z axis side and is grasped by an operator. The movable handle 7 accepts a closing operation and an opening operation, which are user operations made by the operator. Here, the closing control means an operation in which an operator grips the movable handle 7, such as operation unit 72, with a finger while placing the palm of the hand on the handle body 62. In addition, the opening control means an operation of releasing the grasping force of the operator.

FIGS. 1, 3, and 4 illustrate features of the movable handle 7 including a handle base 71, an operation unit 72, and a connecting portion 73.

Handle base 71 is located inside the fixed handle 6. The +Z-axis-side portion of the handle base 71, with respect to the fixed handle 6, is rotatably supported about a first rotational axis Rx1, which is parallel to the Y-axis (FIG. 3). The +Z-axis side of the end portion of the handle base 71 protrudes toward the +Z-axis side, is bifurcated into branches, and functions as an engagement portion 711 for engaging the slider 114 that constitutes the opening and closing mechanism 11. The operation unit 72 is a portion for receiving the operation input by an operator, such as for the closing operation and the opening operation, respectively, and is positioned outside the fixed handle 6 as shown in FIG. 1 and FIG. 4. Connecting portion 73 is a portion for connecting the handle base 71 and the operation unit 72 and is located both inside and outside of the fixed handle 6. When receiving the operation input by an operator for a closing operation, the movable handle 7 rotates counterclockwise around the first rotational axis Rx1. That is, the operation unit 72 moves in a direction toward the handle body 62. On the other hand, when receiving the operation input by an operator for an opening operation, the movable handle 7 rotates clockwise around the first rotational axis Rx1. That is, the operation unit 72 moves in a direction away from the handle body 62.

Here, the second biasing member 16 corresponds to the biasing member according to the present invention. The second biasing member 16, as shown in FIG. 4, is constituted by a coil spring. The second biasing member 16 is supported in the handle body 62 and is engaged with the connecting portion 73. In FIG. 3, the second biasing member 16 biases the movable handle 7 in a direction to rotate clockwise. Note that the range in which the second biasing member 16 acts to rotatably move the handle 7 will be described later in "a range in which the first and second biasing members act."

As shown in FIGS. 1, 3 and 4, switch 8 is provided such that a portion is exposed to the outside from the side surface of the distal end side Ar1 in the handle body 62. The switch 8 is operable by an operator to initiate a treatment operation. The treatment operation includes a procedure that imparts treatment energy to the site of interest.

Rotary knob 9 has a substantially cylindrical shape or conical shape that is coaxial with the central axis Ax, as shown in FIGS. 3 and 4, and is provided on the distal end side Ar1 of the case body 61. The rotary knob 9 accepts a rotation control, which is a user operation by an operator. By the rotation control, the rotary knob 9 rotates about the central axis Ax with respect to the case body 61. Further, in addition to the rotary knob 9 being rotatable, the jaw 12, and the vibration transmission member 13 also can be rotatable about the central axis Ax.

Shaft 10 is a cylindrical pipe made of a material such as metal. Additionally, the outer peripheral surface of the shaft 10 is covered by an electrically insulating outer tube TO (FIG. 2). Further, the end portion of the distal end side Ar1 of the shaft 10 includes a first pin 101 that rotatably supports jaw 12 to rotate around the second rotational axis Rx2. The first pin 101 extends in a direction perpendicular to the central axis Ax (e.g., perpendicular to the plane of the paper in FIGS. 1 and 2). Furthermore, at the end of the distal end side Ar1 of the shaft 10 and to the +Z-axis side of the shaft 10, notches 102 are formed that extend toward the proximal end side Ar2 and opens toward the distal end side Ar1 (FIG. 2).

The jaw 11 has an opening and closing mechanism that causes elements of the jaw 11 to rotate around the second rotational axis Rx2 in response to the opening operation and closing operation affected by manipulation of the movable handle 7 by an operator. Then, by the opening and closing mechanism, the jaw 11 opens and closes with respect to the end portion 131 (hereinafter, referred to as the treatment portion 131 (FIG. 2)) on the distal end side Ar1 of the vibration transmission member 13 and grasps the target site between the jaw and the treatment portion 131.

As shown in FIGS. 2 to 4, the opening and closing mechanism 11 includes an inner pipe 111 (FIGS. 2 and 3), a holding portion 112 (FIG. 3), a slider receiver 113 (FIG. 3), and a slider 114 (FIGS. 3 and 4). The inner pipe 111 is a cylindrical pipe having a smaller diameter than the shaft 10. Further, the inner pipe 111 is coaxial with the shaft 10 is inserted into the shaft 10. In the inner pipe 111, the +Z-axis side of the end portion of the distal end side Ar1 has an arm portion 1111 that extends toward the distal end side Ar1 (FIG. 2). The arm portion 1111 is attached to the jaw 12 by a second pin 121, which is inserted parallel to the second rotary shaft Rx2 (i.e., is oriented parallel to the first pin 101).

Holding portion 112 is constituted by a material having an electrical insulating property, such as a resin, and has a substantially cylindrical shape. The holding portion 112 is inserted into the rotary knob 9 and the case body 61 in a state of straddling the rotary knob 9 and the case body 61 as shown in FIG. 3. The holding portion 112 holds the vibration transmitting member 13 inserted therein. The distal end side Ar1 of the holding portion 112 is mechanically connected to the rotary knob 9 and the shaft 10. That is, in accordance with the rotation control applied to the rotary knob 9 by an operator, the holding portion 112, the shaft 10, the jaw 12, and the vibration transmitting member 13 rotates about the central axis Ax together with the rotary knob 9.

Slider receiver 113 is composed of a material having an electrical insulation property, such as resin, and has a substantially cylindrical shape. The slider receiver 113, while the holding portion 112 is inserted therein, is movably disposed along the central axis Ax with respect to the holding portion 112. Here, the end of the distal end side Ar1 of the slider receiver 113 connects with respect to the end of the proximal end side Ar2 of the inner pipe 111 such that the end of the distal end side Ar1 of the slider receiver 113 is allowed to move along the central axis Ax with respect to the holding portion 112 and the rotation around the central axis Ax is restricted. That is, in response to the rotation of the rotary knob 9 by an operator, the slider receiver 113 and the inner pipe 111 rotate about the central axis Ax together with the rotation knob 9.

The slider 114 has a substantially cylindrical shape and is disposed to be movable along the central axis Ax relative to the slider receiver 113. The slider 114 is engaged with the movable handle 7 (engaging portion 711) as described above.

The opening/closing mechanism 11 operates as described below in response to an operation on the movable handle 7 by an operator.

In response to a closing operation applied to the movable handle 7 by an operator, slider 114 is pushed to the distal end side Ar1 along the central axis Ax by the engaging portion 711. The slider receiver 113 is subjected to a pressing force toward the distal end side Ar1 resulting from the slider 114 movement and as passed through the first biasing member 15 disposed between the slider 114 and the slider receiver 113, causing the slider receiver 113 to move towards the distal end side Ar1 along the central axis Ax. In conjunction with the movement of the slider receiver 113, the inner pipe 111 moves toward the distal end side Ar1 along the central axis Ax. Further, in conjunction with the movement of the inner pipe 111, the arm portion 1111 pushes the second pin 121 toward the distal end side Ar1. Then, the jaw 12 rotates counterclockwise in FIG. 2 about the second rotational axis Rx2. At this time, since the second pin 121 also moves while keeping a constant distance about the second rotational axis Rx2, the arm portion 1111 moves to the distal end side Ar1 while deforming the +Z-axis side notch 102. In other words, the jaw 12 moves in a direction (closing direction) proximate to the treatment portion 131. Further, in accordance with the opening operation to the movable handle 7 by an operator, the jaw 12 in FIG. 2 rotates clockwise around the second rotational axis Rx2. In other words, the jaw 12 moves in a direction (opening direction) spaced apart from the treatment portion 131. As described above, in response to an operation on the movable handle 7 by an operator, the jaw 12 opens and closes with respect to the treatment portion 131 and grasps the target site between the jaw and the treatment portion 131

The first biasing member 15 corresponds to a biasing member according to the present invention. In FIG. 3, the first biasing member 15 is a coil spring. The biasing member 15 acts on the slider 114 to bias the movable handle 7 in a direction to rotate clockwise and adjusts the gripping force for gripping the target site between the jaw 12 and the treatment portion 131. More specifically, the first biasing member 15 is used to make the gripping force constant.

Note that the range in which the first biasing member 15 acts within the movable range in which the movable handle 7 is rotatable will be described in "a range in which the first and second biasing members act" described later.

Jaw 12 corresponds to a second gripping piece according to the present invention. At least a portion of the jaw 12 is made of a conductive material.

The vibration transmission member 13 corresponds to a first gripping piece according to the present invention. The vibration transmission member 13 is composed of a conductive material and has an elongated shape extending linearly along the central axis Ax. Further and as shown in FIG. 2, the treatment portion 131 of the vibration transmission member 13 is located in the inner pipe 111 and projects to the outside. The proximal end side Ar2 of the vibration transmission member 13 mechanically connects to the ultrasonic transducer 5, as shown in FIG. 3. That is, the vibration transmission member 13 transmits the ultrasonic vibration generated by the ultrasonic transducer 5 from the proximal end side Ar2 to the treatment portion 131. In the first embodiment, the ultrasonic vibration is a longitudinal vibration vibrating in a direction along the central axis Ax. In order to ensure electrical insulation between the shaft 10 and the inner pipe 111 and the vibration transmitting member 13, the outer peripheral surface of the vibration transmission member 13 is covered by an electrically insulating inner tube TI (FIG. 2).

The treatment instrument 2 includes an assist system 14 that generates an attracting force, such as a magnetic force, to attract the operation unit 72 with respect to the handle body 62. The assist system 14 assists the closing operation of the movable handle 7 by an operator. Note that a detailed configuration of the assist system 14 will also be described later in "a configuration of an assist system."

The ultrasonic transducer 5 includes a transducer (TD) case 51 and an ultrasonic transducer 52, as shown in FIGS. 1 and 3. TD case 51 supports the ultrasonic vibrator 52 is detachably connected to the case body 61. The ultrasonic vibrator 52 generates ultrasonic vibration under control by the controller 3. In the first embodiment, the ultrasonic vibrator 52 is constituted by a bolt-clamped Langevin transducer (BLT). For convenience of explanation, of the features of the ultrasonic vibrator 52 (BLT), FIG. 3 illustrates only the front mass 521 to be connected to the proximal end side Ar2 of the vibration transmitting member 13.

Composition of the Control Device

Controller 3 collectively control the operation of the treatment instrument 2. Specifically, the controller 3, by passing operating signals through the electrical cable C (FIG. 1), detects the operation of the switch 8 by an operator. Then, when the controller 3 detects the switch operation, operating signals and power are passed through the electric cable C to impart treatment energy to the target site grasped between the jaw 12 and the treatment portion 131. In other words, the controller 3 controls operation of the treatment instrument 2 to treat the target site.

For example, when applying ultrasonic energy to the target site, the controller 3 supplies drive power to the ultrasonic vibrator 52 by passing it through the electrical cable C. Thus, the ultrasonic vibrator 52 generates a longitudinal vibration (ultrasonic vibration) which vibrates in a direction along the central axis Ax. The treatment portion 131 also vibrates at a desired amplitude by the longitudinal vibration. Then, an ultrasonic vibration is applied from the treatment portion 131 to the target site grasped between the jaw 12 and the treatment portion 131. In other words, ultrasonic energy is applied from the treatment portion 131 to the target site.

Further, for example, when imparting high-frequency energy to the target site, the controller 3 to supplies high-frequency power between the jaw 12 and the vibration transmission member 13 by passing through the electric cable C. Thus, a high frequency current flows through the target site grasped between the jaw 12 and the treatment portion 131. In other words, the subject site is imparted with high frequency energy.

Structure of the Assist System

Figure 5:
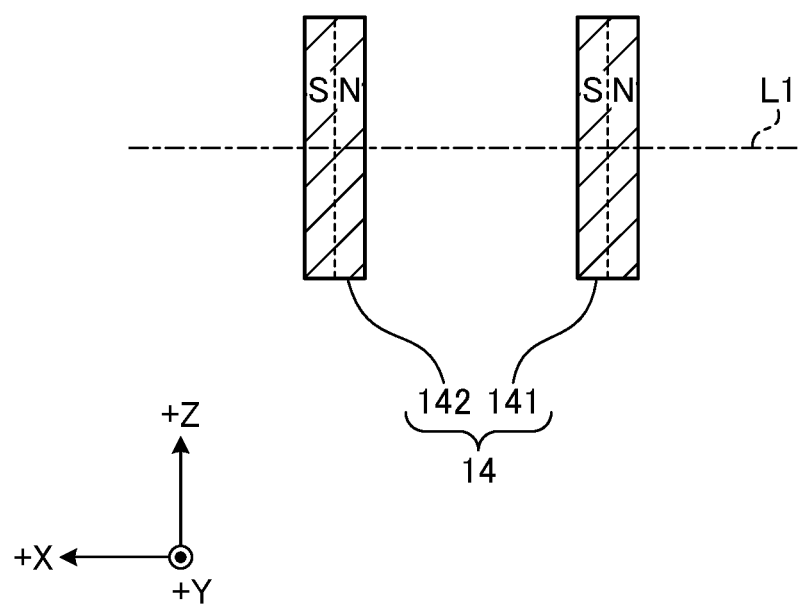
FIG. 5 is a diagram illustrating a configuration of an assist system.

Next, a configuration of the assist system 14 will be described. The assist system 14 includes a first magnet 141 and a second magnet 142, as shown in FIGS. 1 and 5. FIG. 5 is a diagram showing the configuration of the assist system 14. In FIG. 5, line L1 represents the movement of a locus of the second magnet 142, which moves with the operation unit 72 in accordance with the operation of the movable handle 7 by an operator. Further, in FIG. 5, for convenience of explanation, the fixed handle 6 and the movable handle 7 are not shown.

As shown in FIG. 1, the first magnet 141 has the shape of a flat plate or disc and is attached to the side surface of the handle body 62, such as on the distal end side Ar1 at the end of the −Z-axis side of the handle body 62. More specifically and as shown in FIG. 5, the S pole of the first magnet 141 faces the +X-axis side and the magnetizing direction is attached to the handle body 62 in a position along the line L1. Also as shown in FIG. 1, the second magnet 142 is similar to the first magnet 141 and has the shape of a flat plate or disc and is attached to the side surface of the operation unit 72, such as the proximal end side Ar2 at the end of the −Z-axis side of the operation unit 72. More specifically and as shown in FIG. 5, the N pole of the second magnet 142 faces the −X-axis side and the magnetizing direction is attached to the operation unit 72 in a position along the line L1. That is, the S pole of one magnet is arranged so as to face the N pole of the other magnet.

In a state where the operation unit 72 is closest to the handle body 62, the first magnet 141 and second magnet 142 face each other in a direction along the line L1. That is, in the assist system 14, when the operation unit 72 is sufficiently close to the handle body 62, the magnetic forces of the first magnet 141 and second magnet 142 generate a force to attract the operation unit 72 toward to the handle body 62. Further, when the operation unit 72 is closest to the handle body 62, the first magnet 141 and second magnet 142 may be in contact with each other; alternatively, when the operation unit 72 is closest to the handle body 62, the first magnet 141 and second magnet 142 face each other and are separated by a gap having a predetermined size.

Note that details of the adsorption force associated with the assist system 14 will be described later in "adsorption force of the assist system."

Regarding the range in which the first and second biasing members act

Figure 6:
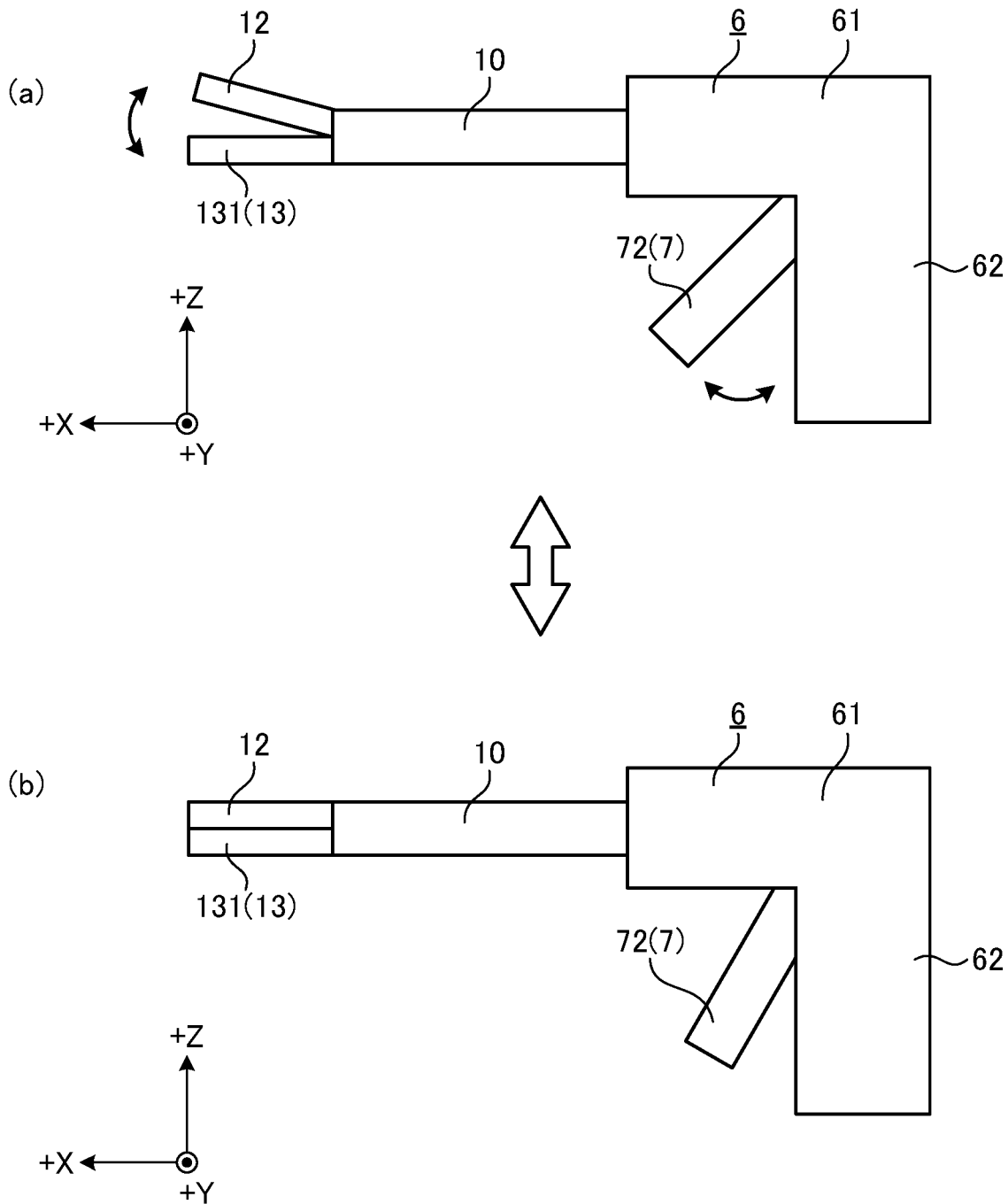
FIG. 6 is a diagram illustrating a range in which the first, second biasing member acts within the movable range in which the movable handle is rotatable.
Figure 7:
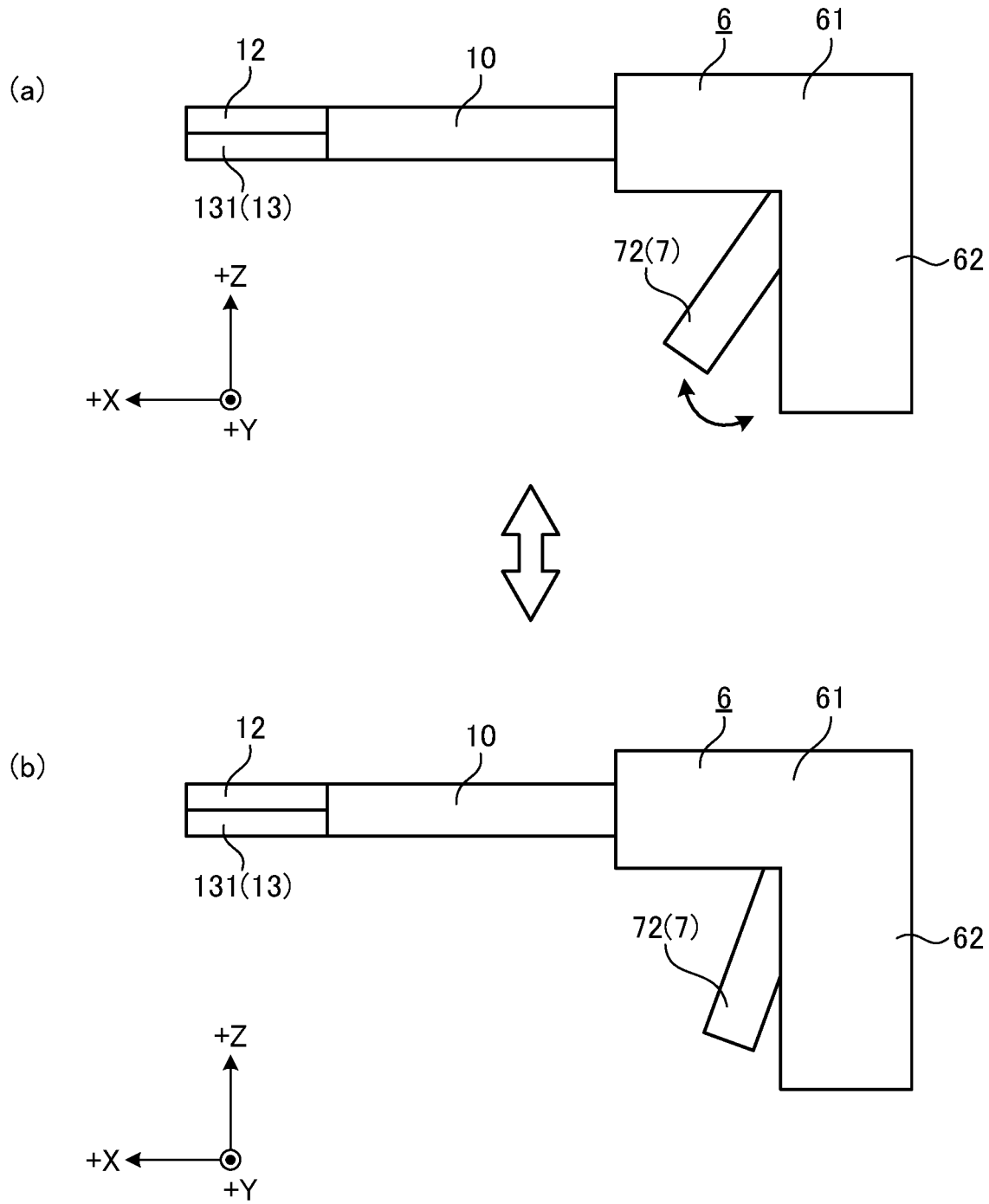
FIG. 7 is a diagram illustrating a range in which the first, second biasing member acts within the movable range in which the movable handle is rotatable.

Next, the movable range in which the movable handle 7 is rotatable and the range(s) in which the first biasing member 15 and second biasing member 16 act will be described. The movable range in which the movable handle 7 is rotatable has two portions—a first movable range and a second movable range. FIG. 6 is a diagram illustrating the first movable range of the movable handle 7 and FIG. 7 is a diagram illustrating a second movable range of the movable handle 7. Incidentally, view (b) in FIG. 6 and view (a) in FIG. 7 show the movable handle 7 in the same position. Different biasing members have effect in different portions of the movable range. For example, the first biasing member 15 acts only in the second movable range of the movable handle 7, while the second biasing member 16 acts in the entire movable range (both the first and second movable ranges) in which the movable handle 7 is rotatable.

Specifically, the first movable range is a range from a state in which the jaw 12 is most spaced apart from the treatment portion 131 (position in view (a) in FIG. 6) to a state in which the jaw 12 is in contact with the treatment portion 131 (position in view (b) in FIG. 6) when nothing is grasped between the jaw 12 and the treatment portion 131. In the first movable range, of the two biasing members (i.e., first biasing member 15 and second biasing member 16), only the second biasing member 16 is operative to bias the movable handle 7 in a direction to rotate clockwise. In example embodiments, the first movable range means a range of 15 to 20 degrees.

Also specifically, the second movable range is a range of movement of the movable handle 7 after the jaw 12 has been brought into contact with the treatment portion 131, i.e., a range of movement of the movable handle 7 from the position shown in view (b) in FIG. 6 and in view (a) in FIG. 7). In the second movable range, the operation unit 72 moves in a direction toward to the handle body 62 (from the position shown in view (b) in FIG. 6 and in view (a) in FIG. 7) toward the handle body 62 in response to an operation on the movable handle 7 by an operator. In other words, the second movable range is a range from a state in which the jaw 12 is brought into contact with the treatment portion 131 (the position shown in view (b) in FIG. 6 and in view (a) in FIG. 7) to a state in which the operation unit 72 is closest to the handle body 62 (the position shown in view (b) in FIG. 7). In the second movable range, both biasing members (i.e., first biasing member 15 and second biasing member 16) are operative to bias the movable handle 7 in a direction to rotate clockwise. In example embodiments, the second movable range means a range of 10 to 15 degrees.

On Attraction Force of Assist System

Figure 8:
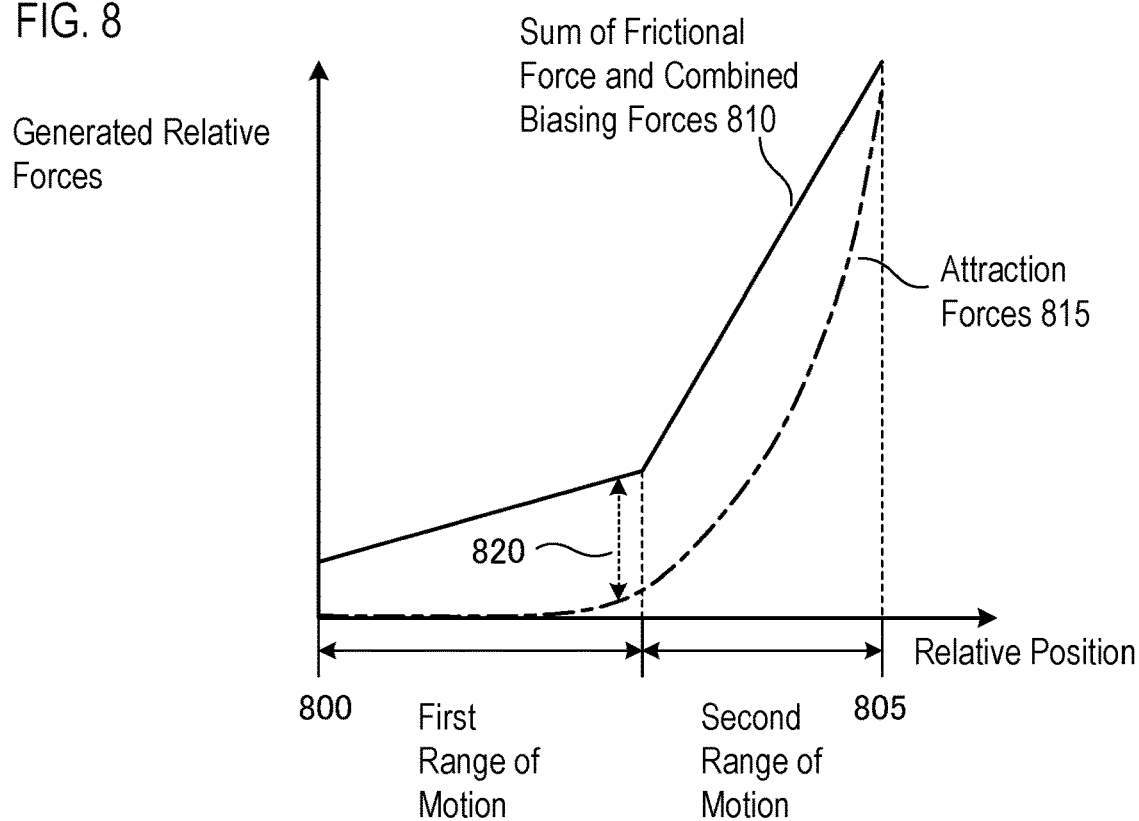
FIG. 8 is a diagram illustrating an adsorption force by an assist system.

Next, an attraction force associated with the assist system 14 will be described. FIG. 8 is a diagram illustrating various forces associated with the movement of the movable handle. In FIG. 8, the horizontal axis shows the relative position of the movable handle 7 as it moves through its range of motion from fully open 800 to fully closed 805, including the first moveable range and the second movable range, and the vertical axis shows the generated relative forces associated with that movement. The generated relative forces include the frictional force acting against the movable handle 7, the combined force of the biasing force from the first biasing member 15 and second biasing member 16, and the attraction forces associated with the assist system 14. In FIG. 8, the sum of the frictional force and the combined biasing forces are represented by solid line 810 and the attraction forces are represented by the dot-dash line 815.

As seen in FIG. 8, as the relative position of the movable handle moves toward the fully closed position 805, e.g., by the operator closing their hand around the handle body 62 and the operation unit 72, i.e., gripping, the generated relative forces increase. Further, the increase in the sum of the frictional force and the combined biasing forces 810 are linear increasing in each of the first range of motion and second range of motion (albeit at different rates), while the increase in the attraction forces 815 is exponentially increasing, overall. The difference (in the generated relative forces) between the sum of the frictional force and the combined biasing forces 810 and the attraction forces 815 represents the grip force 820 that is applied by the operator, e.g., by gripping the handle body 62 and the operation unit 72, in order to close the movable handle 7.

As seen in FIG. 8, the grip force 820 is smaller in the second movable range as compared to the first movable range. It is preferable that the attraction forces 815 in the first movable range is 30% or less of the attraction forces 815 in the second movable range in order to realize a reduction in grip force to the operator. Also, in the first embodiment, the grip force 820 is minimized in a state where the operation unit 72 is closest to the handle body 62, i.e., in the fully closed position 805.

According to the first embodiment described above, the following effects can be achieved. The treatment instrument 2 according to the first embodiment includes the above-described assist system 14. Therefore, even when a first biasing member 15 is provided that makes the gripping force (for grasping the target site between the jaw 12 and the treatment portion 131) constant, it is possible to reduce the force required for the closing operation with respect to the movable handle 7 by the assist system 14. Therefore, according to the treatment instrument 2 of the first embodiment, operability can be improved.

In particular, in the second movable range, the attraction forces 815 resulting from the assist system 14 are smaller than the sum of the frictional force acting on the movable handle 7 and the combined biasing forces from the first and second biasing members 15, 16 to the movable handle 7 (line 810). Therefore, when in the second movable range and an operator releases the grip force from the movable handle 7 (i.e., from the operation unit 72), the jaw 12 opens with respect to the treatment portion 131 because the sum of the frictional force acting on the movable handle 7 and the combined biasing forces from the first and second biasing members 15, 16 is greater than the attraction forces 815 resulting from the assist system 14. As a result, in the second movable range, an operator does not need to apply a force to the movable handle 7 in order to open the movable handle 7. Therefore, operability can be further improved.

Further, the attraction forces resulting from the assist system 14 increases in an exponential manner as the amount of gripping of the handle body 62 and the operation unit 72 by an operator increases, e.g., as the movable handle 7 approaches the fully closed position 805. Therefore, in the first movable range, it is possible to set a state in which the attraction force by the assist system 14 is too small to work. Therefore, in the first movable range, which is a range in which a delicate procedure is performed, the attraction forces by the assist system 14 does not affect the delicate procedure.

In particular, the amount of gripping force when gripping the handle body 62 and the operation unit 72 (corresponding to the difference between the solid line and the dashed line shown in FIG. 8 at a particular relative position) is minimized in the second movable range. More specifically, the amount of gripping force when gripping the handle body 62 and the operation unit 72 is minimized in a state where the operation unit 72 is closest to the handle body 62. Therefore, it is possible to provide a click feeling when the operation unit 72 is closest to the handle body 62. It is simultaneously possible to realize an operability in which the jaw 12 is automatically opened without applying an opening force. Here, the click feeling means that giving an impact of a click to the user when the operation unit 72 is closest to the handle body 62 and the first magnet 141 and the second magnet 142 contact each other strongly. This impact is occurred by rapidly decreasing the amount of gripping force as the gripping amount increases.

Second Embodiment

Next, a second embodiment will be described. In the following description, the same reference numerals will be used for the same configurations as in the first embodiment described above, and detailed description thereof will be omitted or simplified. In the procedure instrument 2 according to the second implementation, the second biasing member 16 is not provided (as it was with respect to the treatment instrument 2 described in the first embodiment described above).

Figure 9:
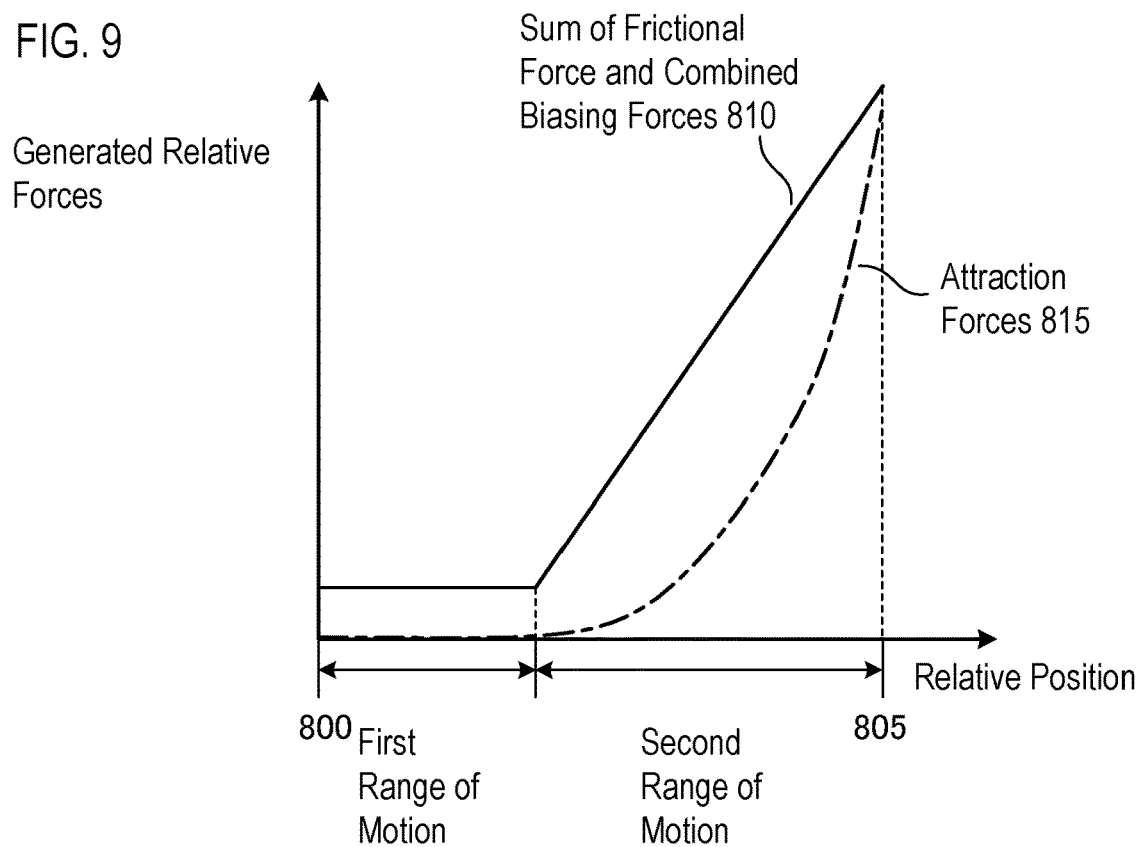
FIG. 9 is a diagram illustrating an adsorption force by an assist system according to the second embodiment.

FIG. 9 is a diagram illustrating various forces associated with the movement of the movable handle in the treatment instrument 2 according to the second implementation. Specifically, FIG. 9 is a diagram showing generated relative forces as a function of relative positions similar to that show in FIG. 8. FIG. 9 shows (in solid line 810) the sum of the frictional force acting on the movable handle 7 and the biasing force from the first biasing member 15 to the movable handle 7 and (in dot-dash line 815) the attraction forces associated with the assist system 14.

Since the second biasing member 16 is not provided in the treatment instrument 2 according to the second embodiment, in the first movable range (First Range of Motion), the sum of the frictional force 810 is only due to the frictional force, which is constant. In the second movable range (Second Range of Motion), the biasing force is applied to the movable handle 7 from the first biasing member 15. Thus, in the second movable range (Second Range of Motion), the sum of the frictional force 810 is due to both the frictional force and the first biasing member 15.

According to the second embodiment, the attraction forces by the assist system 14 is smaller than the combined force of the frictional force acting on the movable handle 7 and the urging force from the first biasing member 15 to the movable handle 7 during the movement of the movable handle 7 in both of the first and second movable ranges, as shown by dot-dash line 815 in FIG. 9. This relative relationships is similar as in the first embodiment described above and, even when the second biasing member 16 is omitted as in the second embodiment, the same effect as in the first embodiment described above is achieved.

In the second embodiment described above, the second biasing member 16 has been omitted, but the present invention is not limited thereto, and the biasing member according to the present invention may be configured only by the first biasing member 15.

Third Embodiment

Next, a third embodiment will be described. In the following description, the same reference numerals will be used for the same configurations as in the first embodiment described above, and detailed description thereof will be omitted or simplified. In the treatment instrument 2 according to the third embodiment, the configuration of the assist system 14 is changed with respect to the treatment instrument 2 described in the first embodiment. Hereinafter, for convenience of explanation, the assist system according to the third embodiment will be described as an assist system 14A.

Figure 10:
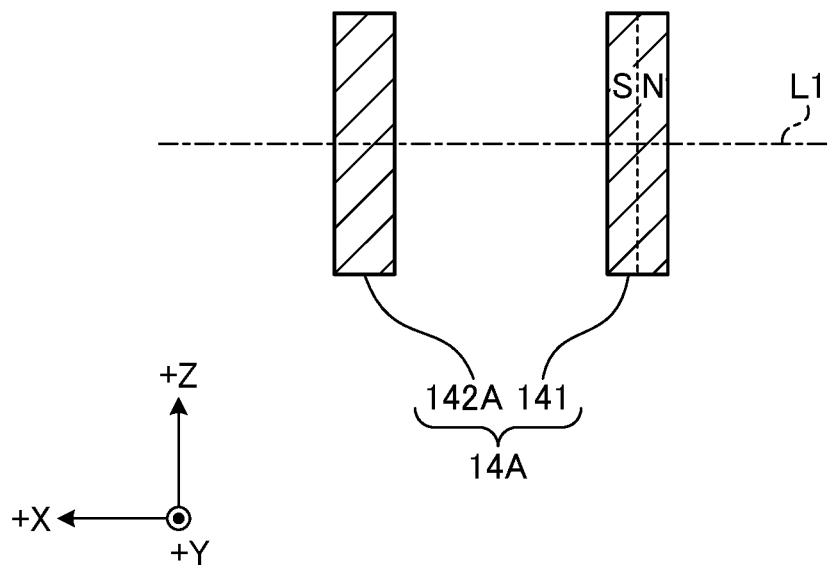
FIG. 10 is a diagram showing a configuration of an assist system according to the third embodiment.

FIG. 10 is a diagram illustrating a configuration of an assist system 14A according to the third embodiment. Specifically, FIG. 10 is a view corresponding to FIG. 5. The assist system 14A shown in FIG. 10 is similar to the assist system 14 described in the first embodiment, except that the assist system 14A in the third embodiment employs a ferromagnetic 142A instead of the second magnet 142 (as in the assist system 14 of the first embodiment shown in FIG. 5). Even when the assist system 14A according to the third embodiment is employed, the same effect as from the assist system 14 of the first embodiment is achieved.

Note that, in the assist system 14A according to the third embodiment, a ferromagnetic 142A is employed instead of the second magnet 142 as in the assist system 14 described in the first embodiment, but the present invention is not limited thereto. Additionally, in the third embodiment, a ferromagnetic material may be used in place of the first magnet 141 (rather than the second magnet 142), to similar effect.

Fourth Embodiment

Next, a fourth embodiment will be described. In the following description, the same reference numerals will be used for the same configurations as in the first embodiment described above, and detailed description thereof will be omitted or simplified. In the treatment instrument 2 according to the fourth embodiment, the configuration of the assist system 14 is changed with respect to the treatment instrument 2 described in the first embodiment described above. Hereinafter, for convenience of explanation, the assist system according to the fourth embodiment will be described as an assist system 14B.

Figure 11:
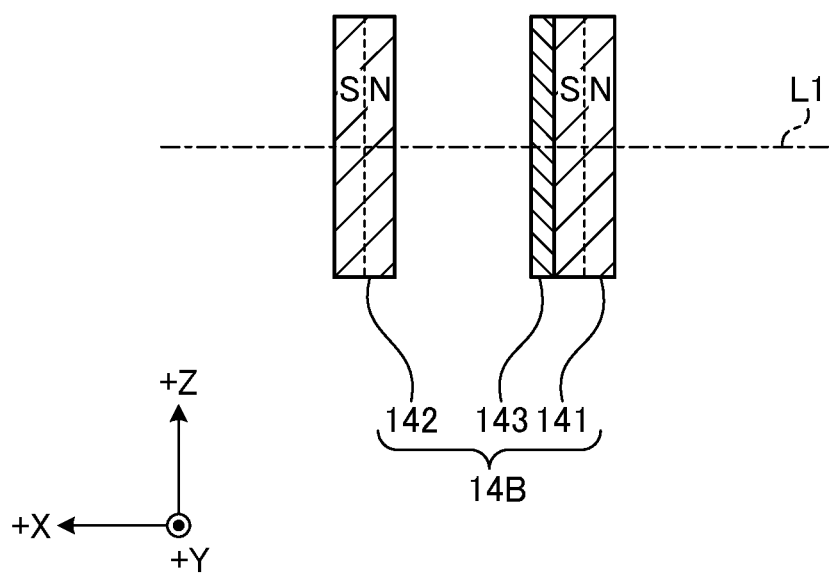
FIG. 11 is a diagram showing a configuration of an assist system according to the fourth embodiment.

FIG. 11 is a diagram illustrating the configuration of the assist system 14B according to the fourth embodiment. Specifically, FIG. 11 is a view corresponding to FIG. 5. The assist system 14B shown in FIG. 11 is similar to the assist system 14 described in the first embodiment, except that in the assist system 14B and as shown in FIG. 11, an impact alleviation member 143 is added to the assist system 14.

The impact alleviation member 143 mitigates the impact when the operation unit 72 is closest to the handle body 62. As shown in FIG. 11, the impact alleviation member 143 is constructed of an elastomeric material, such as silicone rubber, or an elastic body, such as a spring, and is attached to a surface of the first magnet 141 facing the second magnet 142. In alternative embodiments, the impact alleviation member 143 is attached to a surface of the second magnet 142 facing the first magnet 141.

According to the fourth embodiment, in addition to the effects similar to those of the first embodiment, the following effects can be obtained. In the treatment instrument 2 according to the first embodiment, in a state in which the operation unit 72 is closest to the handle body 62, when the first and second magnets 141,142 are configured to be in contact with each other, there is a case where the tip of the treatment instrument 2 is shifted from a desired position by an impact when the first and second magnets 141,142 are brought into contact with each other. On the other hand, in the treatment instrument 2 according to the fourth embodiment, the above-described impact alleviation member 143 is provided. Therefore, the impact when the operation unit 72 is closest to the handle body 62 is alleviated by the impact alleviation member 143, and it is possible to suppress any shifting of the tip of the treatment instrument 2 from the desired position.

Fifth Embodiment

Next, a fifth embodiment will be described. In the following description, the same reference numerals will be used for the same configurations as in the fourth embodiment, and detailed description thereof will be omitted or simplified. In the treatment instrument 2 according to the fifth embodiment, the configuration of the assist system 14B is changed with respect to that of the treatment instrument 2 described in the fourth embodiment. Hereinafter, for convenience of explanation, the assist system according to the fifth embodiment will be described as an assist system 14C.

Figure 12:
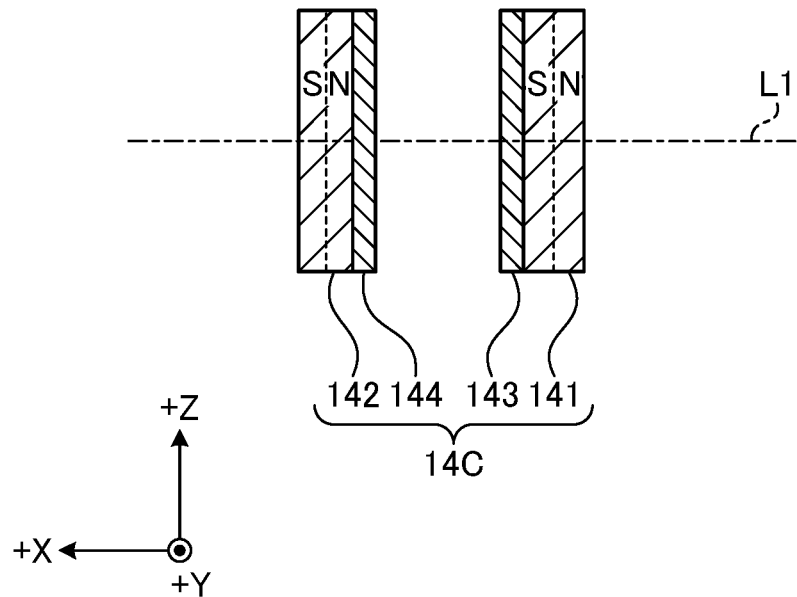
FIG. 12 is a diagram showing a configuration of an assist system according to the fifth embodiment.

FIG. 12 is a diagram illustrating a configuration of an assist system 14C according to the fifth embodiment. Specifically, FIG. 12 is a view corresponding to FIG. 5. As shown in FIG. 12, in the assist system 14C an additional impact alleviation member 144 is added to the assist system 14B as described in the fourth embodiment. In other words, the assist system 14C in the fifth embodiment includes a first impact alleviation member 143 on a first magnet 141 and a second impact alleviation member 144 on a second magnet 142.

As shown in FIG. 12, second impact alleviation member 144 is constituted by a material similar to the first impact alleviation member 143 and is attached to the surface of the second magnet 142 and facing the first impact alleviation member 143. Then, the second impact alleviation member 144, together with the impact mitigating member 143, mitigates the impact when the operation unit 72 is closest to the handle body 62. Even when the assist system 14C according to the fifth embodiment is employed, the same effect as in the fourth embodiment is achieved.

Sixth Embodiment

Next, a sixth embodiment will be described. In the following description, the same reference numerals will be used for the same configurations as in the first embodiment described above, and detailed description thereof will be omitted or simplified. In the treatment instrument 2 according to the sixth embodiment, the configuration of the assist system 14 is changed with respect to that of the treatment instrument 2 described in the first embodiment. Hereinafter, for convenience of explanation, the assist system according to the sixth embodiment will be described as an assist system 14D.

Figure 13:
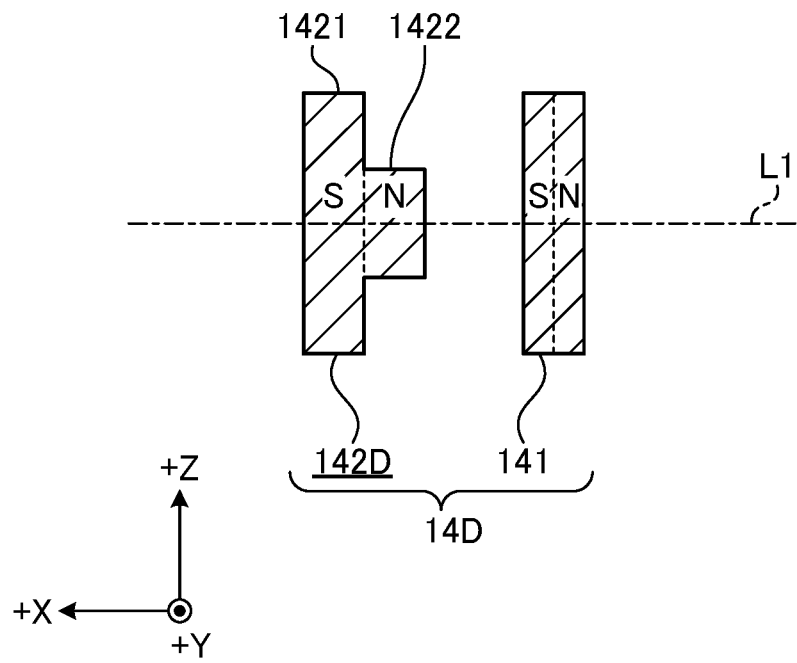
FIG. 13 is a diagram showing a configuration of an assist system according to a sixth embodiment.

FIG. 13 is a diagram illustrating a configuration of an assist system 14D according to the sixth embodiment. Specifically, FIG. 13 is a view corresponding to FIG. 5. The assist system 14D shown in FIG. 13 is similar to the assist system 14 described in the first embodiment, except that in the assist system 14D and as shown in FIG. 12, the shape of the second magnet 142 is different. Hereinafter, for convenience of explanation, a second magnet according to the sixth embodiment will be described as a second magnet 142D.

As shown in FIG. 13, the second magnet 142D includes a flat base portion 1421 and a convex portion 1422 that protrudes toward the first magnet 141 from a substantially central portion of the surface in the base portion 1421 facing the first magnet 141. In the sixth embodiment, the second magnet 142D consists of one component.

According to the sixth embodiment, in addition to the effects similar to those of the first embodiment, the following effects can be obtained. In the assist system 14D, the second magnet 142D comprises a convex portion 1422 as described above. Therefore, the attraction forces due to the assist system 14D increase linearly in proportion to the amount of gripping of the handle body 62 and the operation unit 72 by an operator. Therefore, when the operation unit 72 is close to the handle body 62, the magnetic force due to the assist system 14D is prevented from increasing rapidly in the second range of motion, which can prevent the operation unit 72 from unintentionally moving in the closing direction. However, the magnetic force due to the assist system 14D is increased in the first range of motion, which can affect the moving of the operation unit 72 with respect to the handle body 62 when the operation unit 72 is spaced apart from the handle body 62.

Seventh Embodiment

Next, a seventh embodiment will be described. In the following description, the same reference numerals will be given to the same configurations as in the sixth embodiment, and detailed description thereof will be omitted or simplified. In the treatment instrument 2 according to the seventh embodiment, the configuration of the assist system 14D is changed with respect to the treatment instrument 2 described in the sixth embodiment. Hereinafter, for convenience of explanation, the assist system according to the seventh embodiment will be described as an assist system 14E.

Figure 14:
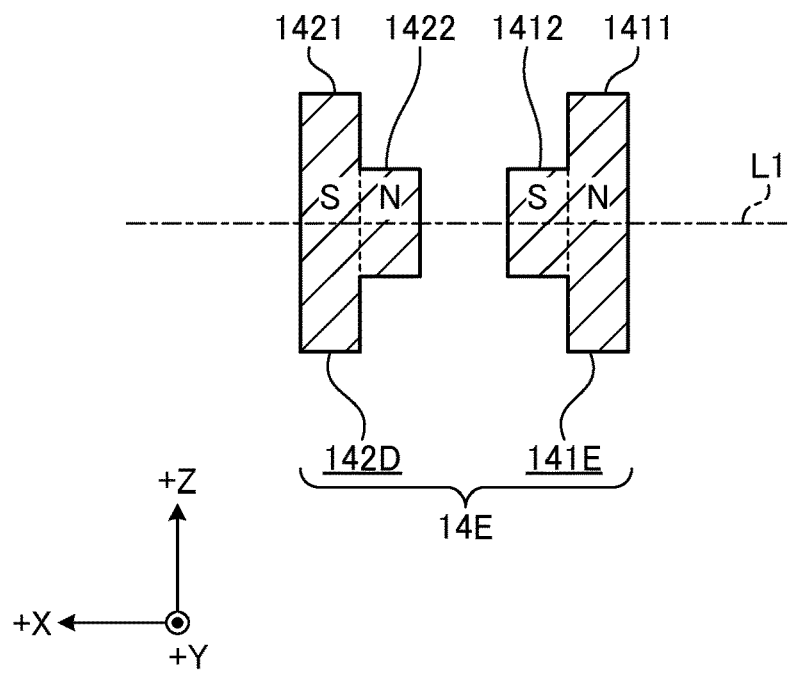
FIG. 14 is a diagram illustrating a configuration of an assist system according to the seventh embodiment.

FIG. 14 is a diagram illustrating a configuration of an assist system 14E according to the seventh embodiment. Specifically, FIG. 14 is a view corresponding to FIG. 5. The assist system 14E shown in FIG. 14 is similar to the assist system 14D described in the sixth embodiment, except that in the assist system 14E and as shown in FIG. 14, the shape of the first magnet 141 is changed (in addition to the shape of the second magnet 142D). Hereinafter, for convenience of explanation, the first magnet according to the seventh embodiment will be described as a first magnet 141E. In other words, the assist system 14D in the seventh embodiment includes a first magnet 141E with a convex portion and a second magnet 142D with a convex portion.

As shown in FIG. 14, the first magnet 141E has the same shape as the second magnet 142D. That is, the first magnet 141E includes a flat base portion 1411, and a convex portion 1412 protruding toward the second magnet 142D from a substantially central portion of the surface in the base portion 1411 facing the second magnet 142D. In the seventh embodiment, the first magnet 141E consists of one component.

Even when the assist system 14E according to the seventh embodiment described above is employed, the same effect as for the assist system 14D in the sixth embodiment is achieved. Incidentally, in the assist system 14E according to seventh embodiment, a second magnet 142 may be employed as described in the first embodiment instead of the second magnet 142D.

Eighth Embodiment

Next, an eighth embodiment will be described. In the following description, the same reference numerals will be given to the same configurations as in sixth embodiment, and detailed description thereof will be omitted or simplified. In the treatment instrument 2 according to the eighth embodiment, the configuration of the assist system is changed with respect to the assist system 14D described in the sixth embodiment. Hereinafter, for convenience of description, the assist system according to the eighth embodiment will be described as an assist system 14F.

Figure 15:
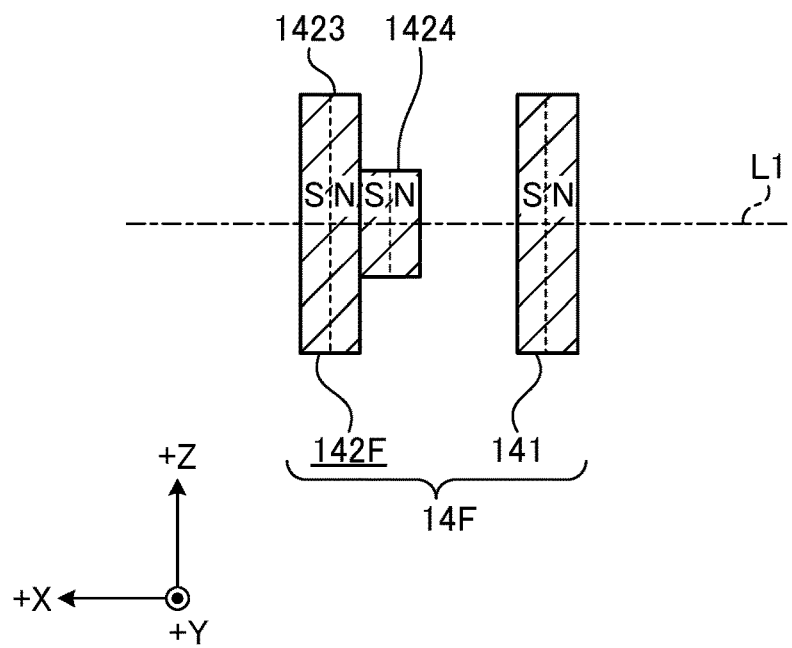
FIG. 15 is a diagram showing a configuration of an assist system according to the eighth embodiment.

FIG. 15 is a diagram showing a configuration of an assist system 14F according to the eighth embodiment. Specifically, FIG. 15 is a view corresponding to FIG. 5. The assist system 14F shown in FIG. 15 is similar to the assist system 14D described in the sixth embodiment, except that the configuration of the second magnet 142D in the assist system 14F shown in FIG. 15 is changed. Hereinafter, for convenience of description, the second magnet according to the eighth embodiment will be referred to as a second magnet 142F.

As shown in FIG. 15, the second magnet 142F has the same general configuration as the second magnet 142D described in the sixth embodiment, except that the base portion and the convex portion in the second magnet 142F are formed separately and are joined to each other. Hereinafter, for convenience of description, the base portion according to the eighth embodiment is described as the base portion 1423, and the convex portion according to the eighth embodiment is described as the convex portion 1424. The base portion 1423 and the convex portion 1424 are joined to each other with the respective S poles of each facing the +X-axis side, i.e., the S poles facing away from the first magnet 141.

When the assist system 14F according to the eighth embodiment described above is employed, the same effect as in the sixth embodiment described above is achieved.

Ninth Embodiment

Next, a ninth embodiment will be described. In the following description, the same reference numerals will be given to the same configurations as in the seventh embodiment described above, and detailed description thereof will be omitted or simplified. In the treatment instrument 2 according to the ninth embodiment, the configuration of the assist system is changed with respect to the assist system 14E described in the seventh embodiment. Hereinafter, for convenience of explanation, the assist system according to the ninth embodiment will be described as an assist system 14G.

Figure 16:
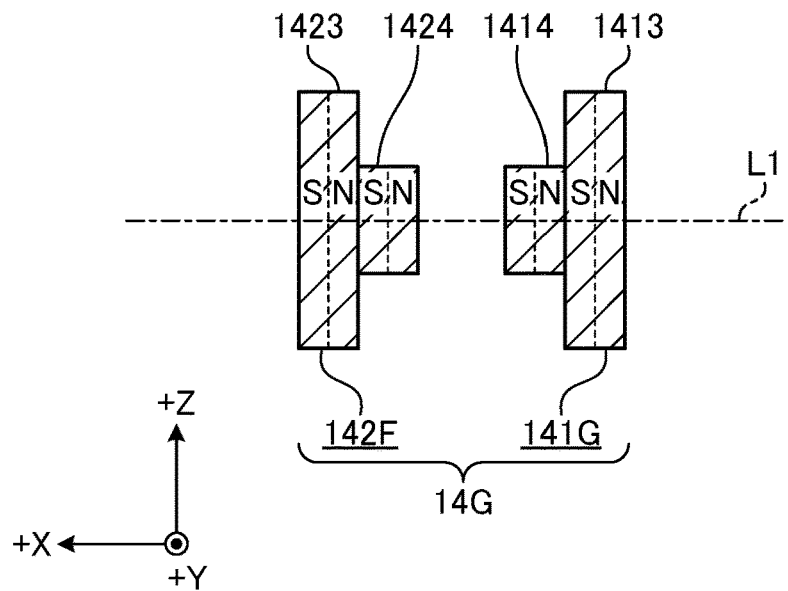
FIG. 16 is a diagram illustrating a configuration of an assist system according to the nineth embodiment.

FIG. 16 is a diagram illustrating a configuration of an assist system 14G according to the ninth embodiment. Specifically, FIG. 16 is a view corresponding to FIG. 5. The assist system 14G shown in FIG. 16 is similar to the assist system 14E described in the seventh embodiment, except that in the assist system 14G shown in FIG. 16, the configuration of the first magnet and the second magnet are different. Specifically, in the assist system 14G, in addition to a second magnet 142F as described in the eighth embodiment, the first magnet is configured similar to second magnet 142F, e.g., with base portion and convex portion formed separately and joined to each other. Hereinafter, for convenience of explanation, the first magnet according to the ninth embodiment will be described as a first magnet 141G and, in the first magnet 141G, a base portion according to the ninth embodiment will be described as a base portion 1413 and a convex portion according to the ninth embodiment will be described as a convex portion 1414. In the first magnet 141G, the base portion 1413 and the convex portion 1414 are joined to each other with the respective S poles of each facing the +X-axis side, i.e., the S poles facing toward the second magnet 142F. Note in the assist system 14G, the S Poles in the first magnet 141G are oriented in the same direction as the S Poles in the second magnet 142F Even when the assist system 14G according to the ninth embodiment described above is employed, the same effect as in the seventh embodiment described above is achieved.

In an alternative embodiment, the assist system 14G according to ninth embodiment described above, may employ the second magnet 142 as described in the first embodiment instead of the second magnet 142F.

Tenth Embodiment

Next, the tenth embodiment will be described. In the following description, the same reference numerals will be given to the same configurations as in the sixth embodiment described above, and detailed description thereof will be omitted or simplified. In the treatment instrument 2 according to the tenth embodiment, the configuration of the assist system is changed with respect to the assist system 14D described in the sixth embodiment. Hereinafter, for convenience of description, the assist system according to the tenth embodiment will be described as an assist system 14H.

Figure 17:
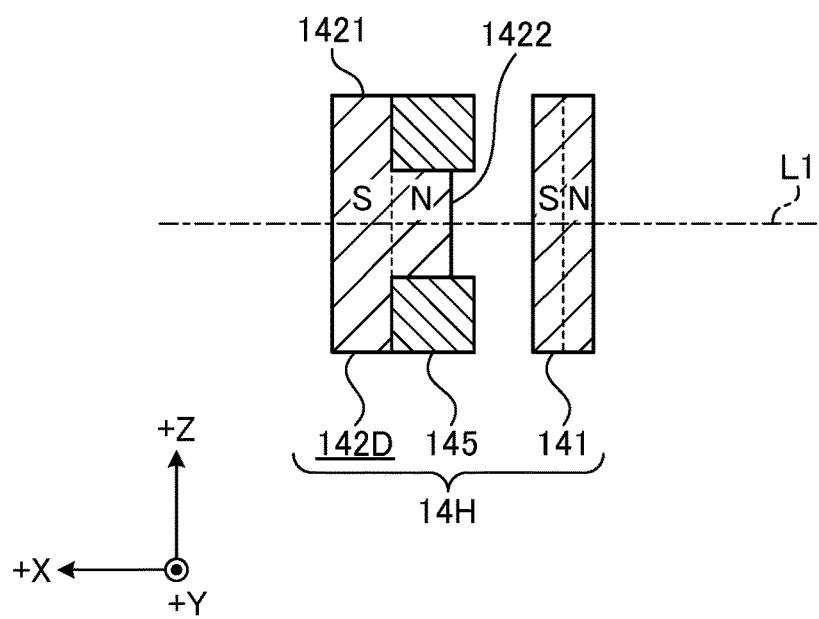
FIG. 17 is a diagram illustrating a configuration of an assist system according to the tenth embodiment.

FIG. 17 is a diagram illustrating a configuration of an assist system 14H according to the tenth embodiment. Specifically, FIG. 17 is a view corresponding to FIG. 5. The assist system 14H shown in FIG. 17 is similar to the assist system 14D described in the sixth embodiment, except that in the assist system 14H shown in FIG. 17, an impact alleviation member 145 is added to the assist system. The impact alleviation member 145 is constituted by an elastomeric material, such as silicone rubber, or an elastic body, such as a spring, and has a shape, such as a cylindrical shape, in which the convex portion 1422 can be located. Further and as shown in FIG. 17, the impact alleviation member 145 is attached to the surface of the base portion 1421 facing the first magnet 141 and the convex portion 1422 is located in the impact alleviation member 145. In this state, the impact alleviation member 145 protrudes further toward the first magnet 141 than the convex portion 1422. As a result, the impact alleviation member 145 mitigates the impact when the operation unit 72 is closest to the handle body 62.

Even when the assist system 14H according to the tenth embodiment is employed, the same effect as in the fourth and sixth embodiments is achieved.

Eleventh Embodiment

Next, the eleventh embodiment will be described. In the following description, the same reference numerals will be given to the same configurations as in seventh embodiment described above, and detailed description thereof will be omitted or simplified. In the treatment instrument 2 according to the eleventh embodiment, the configuration of the assist system is changed with respect to the assist system 14E described in the seventh embodiment. Hereinafter, for convenience of explanation, the assist system according to the seventh embodiment will be described as an assist system 14I.

Figure 18:
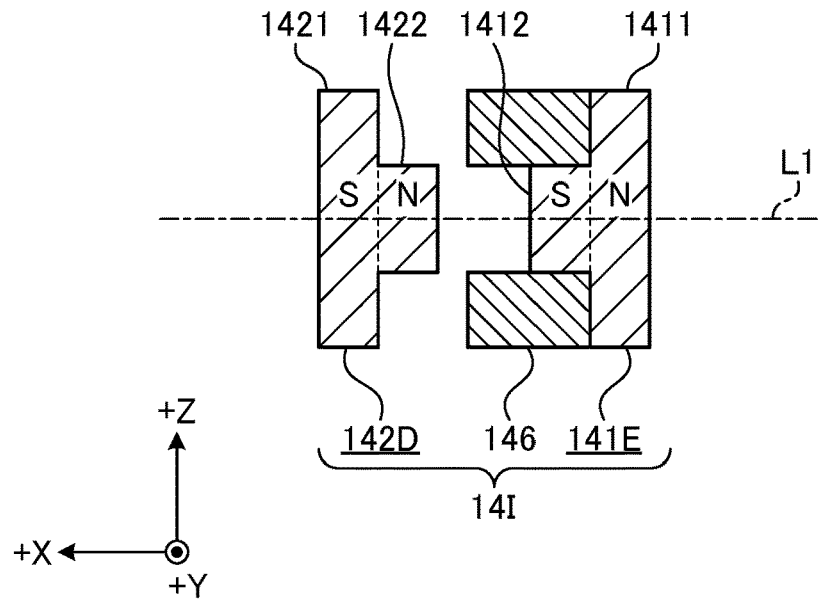
FIG. 18 is a diagram illustrating a configuration of an assist system according to the eleventh embodiment.

FIG. 18 is a diagram illustrating a configuration of an assist system 14I according to the eleventh embodiment. Specifically, FIG. 18 is a view corresponding to FIG. 5. The assist system 14I shown in FIG. 18 is similar to the assist system 14E described in the seventh embodiment, except that in the assist system 14I shown in FIG. 18, an impact alleviation member 146 is added to the assist system 14E described in the seventh embodiment. The impact alleviation member 146 is constituted by an elastomeric material, such as silicone rubber, or an elastic body, such as a spring, and has a shape, such as a cylindrical shape, in which the convex portion 1412 can be located. Further and as shown in FIG. 18, the impact alleviation member 146 is attached to the surface of the base portion 1411 facing the second magnet 142D and the convex portion 1412 is located in the impact alleviation member 146. In this state, the impact alleviation member 146 protrudes further toward the second magnet 142D than the convex portion 1412. As a result, the impact alleviation member 146 mitigates the impact when the operation unit 72 is closest to the handle body 62.

Even when the assist system 14I according to the eleventh embodiment described above is employed, the same effect as in the fourth and seventh embodiments described above is achieved.

Twelfth Embodiment

Next, a twelfth embodiment will be described. In the following description, the same reference numerals will be used for the same configurations as in eighth embodiment described above, and detailed description thereof will be omitted or simplified. In the treatment instrument 2 according to the twelfth embodiment, the configuration of the assist system is changed with respect to the assist system 14F described in the eighth embodiment described above. Hereinafter, for convenience of description, the assist system according to the twelfth embodiment will be described as an assist system 14J.

Figure 19:
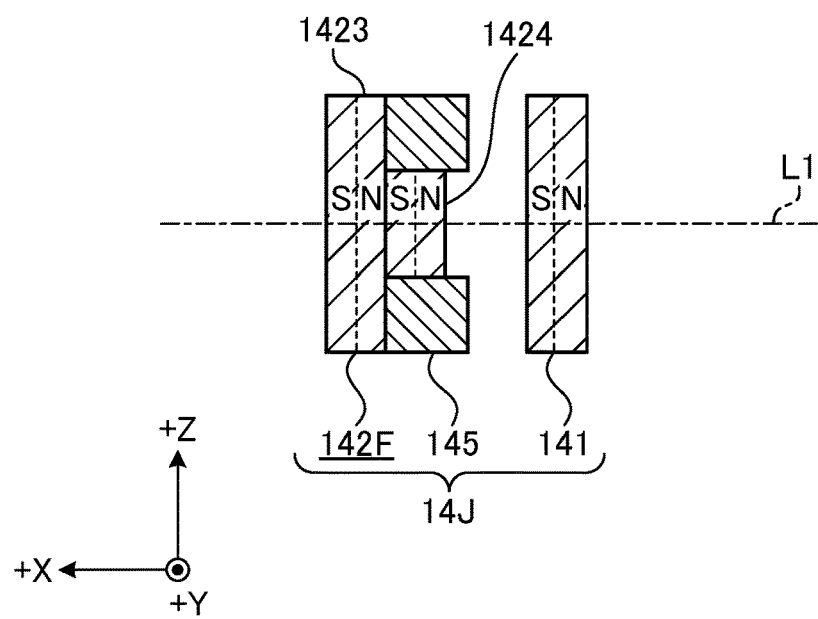
FIG. 19 is a diagram illustrating a configuration of an assist system according to the twelfth embodiment.

FIG. 19 is a diagram illustrating a configuration of an assist system 14I according to the twelfth embodiment. Specifically, FIG. 19 is a view corresponding to FIG. 5. The assist system 14J shown in FIG. 19 is similar to the assist system 14F described in the eighth embodiment, except that the assist system 14J shown in FIG. 19 includes an impact alleviation member 145 as described in the tenth embodiment 10. As shown in FIG. 19, the impact alleviation member 145 is attached to the surface of the base portion 1423 facing the first magnet 141 and the convex portion 1424 is located in the impact alleviation member 145. In this state, the impact alleviation member 145 protrudes further toward the first magnet 141 than the convex portion 1424. As a result, the impact alleviation member 145 mitigates the impact when the operation unit 72 is closest to the handle body 62.

Even when the assist system 14J according to the twelfth embodiment described above is employed, the same effect as in the fourth and eighth embodiments described above is achieved.

Thirteenth Embodiment

Next, a thirteenth embodiment will be described. In the following description, the same reference numerals will be given to the same configurations as in the ninth embodiment described above, and detailed description thereof will be omitted or simplified. In the treatment instrument 2 according to the thirteenth embodiment, the configuration of the assist system is changed with respect to the assist system 14G described in the ninth embodiment. Hereinafter, for convenience of description, the assist system according to the thirteenth embodiment will be described as an assist system 14K.

Figure 20:
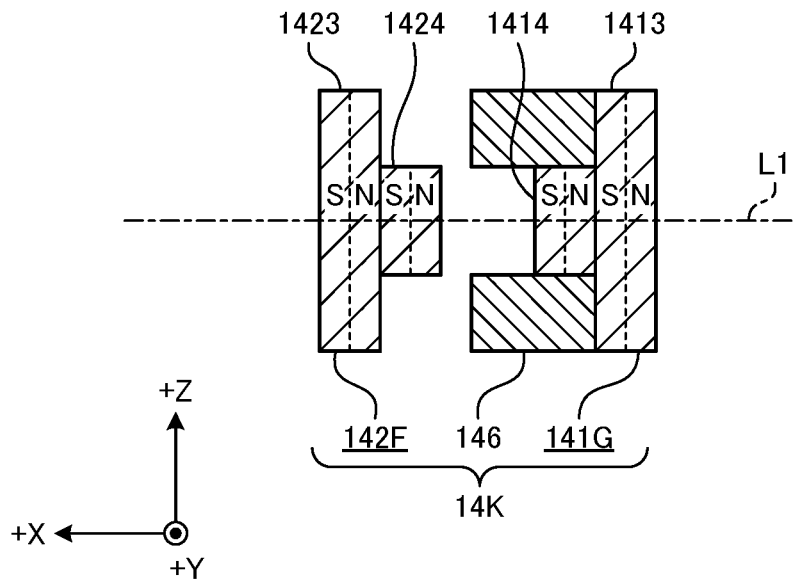
FIG. 20 is a diagram illustrating a configuration of an assist system according to the thirteenth embodiment.

FIG. 20 is a diagram showing the configuration of the assist system 14K according to the thirteenth embodiment. Specifically, FIG. 20 is a view corresponding to FIG. 5. The assist system 14K shown in FIG. 20 is similar to the assist system 14G described in the ninth embodiment, except the assist system 14K shown in FIG. 20 includes an impact alleviation member 146 as described in the eleventh embodiment. As shown in FIG. 20, the shock mitigating member 146 is attached to a surface of the base 1413 facing the second magnet 142F and the convex portion 1414 is located in the shock mitigating member 146. In this state, the shock mitigating member 146 protrudes further toward the second magnet 142F than the convex portion 1414. As a result, the impact alleviation member 146 mitigates the impact when the operation unit 72 is closest to the handle body 62.

Even when the assist system 14K according to the thirteenth embodiment described above is employed, the same effect as in the fourth and ninth embodiments described above is achieved.

In alternative embodiments of the assist system 14K according to thirteenth embodiment described above, the second magnet 142 described in the first embodiment may be employed instead of the second magnet 142F.

Fourteenth Embodiment

Next, the fourteenth embodiment will be described. In the following description, the same reference numerals will be used for the same configurations as in the first embodiment described above, and detailed description thereof will be omitted or simplified. In the treatment instrument 2 according to the fourteenth embodiment, the arrangement of the assist system is changed with respect to assist system 14 described in the first embodiment. Hereinafter, for convenience of description, the assist system according to the fourteenth embodiment will be described as an assist system 14L.

Figure 21:
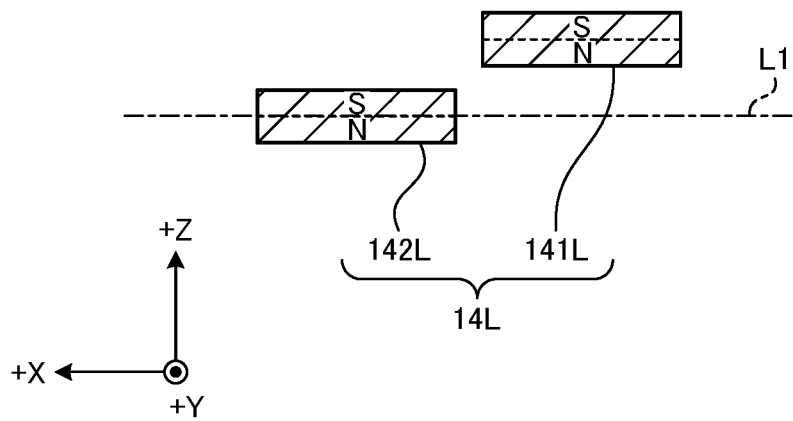
FIG. 21 is a diagram illustrating a configuration of an assist system according to the fourteenth embodiment.

FIG. 21 is a diagram showing a configuration of an assist system 14L according to the fourteenth embodiment. Specifically, FIG. 21 is a view corresponding to FIG. 5. The assist system 14L shown in FIG. 21 is similar to the assist system 14 described in the first embodiment, except that in the assist system 14L shown in FIG. 21, the position and orientation of the first magnet 141 and the second magnet 142 are changed. Hereinafter, for convenience of description, the first magnet according to the fourteenth embodiment will be referred to as a first magnet 141L, and the second magnet according to the fourteenth embodiment will be referred to as a second magnet 142L.

As shown in FIG. 21, the first magnet 141L is attached to the handle main body 62 in a position in which the N-pole faces the −Z-axis side and the magnetization direction crosses the line L1 in a state substantially orthogonal to the line L1. Also as shown in FIG. 21, the second magnet 142L is attached to the operation unit 72 in a position in which the north pole faces the −Z axis side and the magnetization direction crosses the line L1 in a state substantially orthogonal thereto. Then, in a condition where the operation unit 72 is closest to the handle body 62, the first magnet 141L and the second magnet 142L face each other in a state of being spaced apart by a predetermined gap in a direction perpendicular to the line L1. In this configuration, as the operation unit 72 moves close to the handle body 62, the assist system 14L creates a force, i.e., a magnetic force, to attract the operation unit 72 with respect to the handle body 62.

According to the fourteenth embodiment described above, in addition to the effects similar to those of the first embodiment described above, the following effects can be obtained. The treatment instrument 2 according to the fourteenth embodiment includes the above-described assist system 14L. Therefore, it is possible to easily adjust the range given by the attraction force by the assist system 14L. More specifically, in the first movable range, which is a range in which a delicate procedure is performed, the effect of the attraction force by the assist system 14L on the delicate treatment can be substantially set to zero.

Fifteenth Embodiment

Next, the fifteenth embodiment will be described. In the following description, the same reference numerals will be used for the same configurations as in the fourteenth embodiment described above, and detailed description thereof will be omitted or simplified. In the treatment instrument 2 according to the fifteenth implementation, the configuration of the assist system is changed with respect to the assist system 14L described in the fourteenth embodiment. Hereinafter, for convenience of explanation, the assist system according to the fifteenth embodiment will be described as an assist system 14M.

Figure 22:
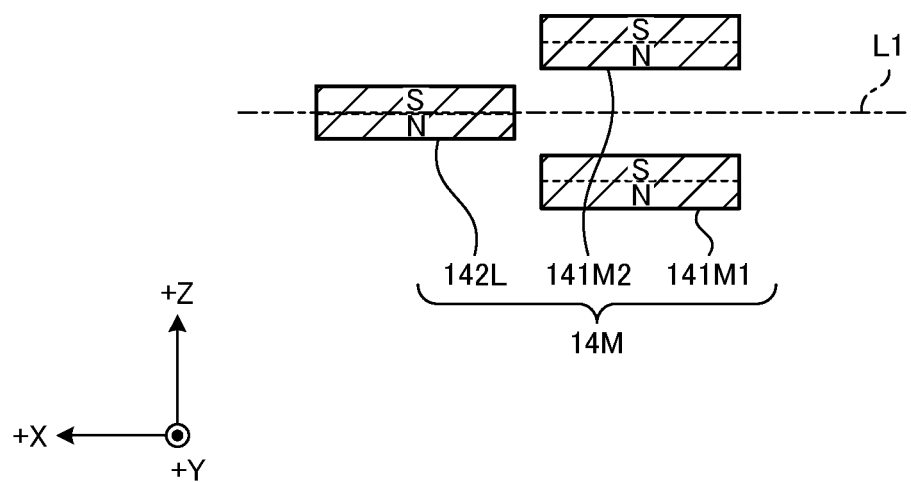
FIG. 22 is a diagram illustrating a configuration of an assist system according to the fifteenth embodiment.

FIG. 22 is a diagram illustrating a configuration of an assist system 14M according to the fifteenth embodiment. Specifically, FIG. 22 is a view corresponding to FIG. 5. The assist system 14M shown in FIG. 22 is similar to the assist system 14L described in the fourteenth embodiment, except that in the assist system 14M shown in FIG. 22 the first magnet 141L is configured as two magnets (rather than as a single first magnet 141L as in the assist system 14L described in the fourteenth embodiment. Hereinafter, for convenience of explanation, the first magnet according to the fifteenth embodiment will be described as a first magnet 141M1, 141M2, which form a pair.

As shown in FIG. 22, in each of the first magnet 141M1, 141M2 of the pair, the N pole faces the −Z-axis side, in a position intersecting in a state where the magnetizing direction is substantially perpendicular to the line L1 at a predetermined distance across the line L1. The first magnet 141M1, 141M2 is attached to the handle body 62 in a this state of being spaced. In a state in which the operation unit 72 is closest to the handle main body 62, the second magnet 142L is positioned between the pair of first magnets 141M1, 141M2 and faces the pair of first magnets 141M1,141M2 with a predetermined gap therebetween perpendicular to the line L1. In other words, in the assist system 14M, an attraction force for attracting the operation unit 72 to the handle 62 by a magnetic force is increased with respect to the assist system 14L described in the fourteenth embodiment described above.

Even when the assist system 14M according to the fifteenth embodiment described above is employed, the same effect as in the fourteenth embodiment described above is achieved.

In an alternative embodiment of the assist system 14M according to fifteenth embodiment described above, the pair of first magnets 141M1, 141M2 may be attached to the operation unit 72 side, and the second magnets 142L may be attached to the handle main body 62 side.

Sixteenth Embodiment

Next, the sixteenth embodiment will be described. In the following description, the same reference numerals will be used for the same configurations as in fourteenth embodiment described above, and detailed description thereof will be omitted or simplified. In the treatment instrument 2 according to the sixteenth embodiment, the arrangement of the assist system is changed with respect to the assist system 14L described in the fourteenth embodiment. Hereinafter, for convenience of description, the assist system according to the sixteenth embodiment will be described as an assist system 14N.

Figure 23:
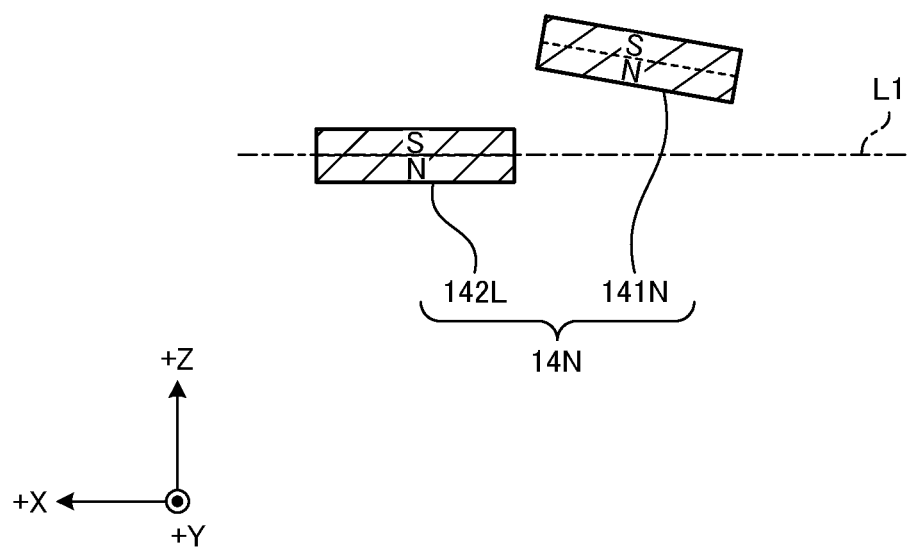
FIG. 23 is a diagram illustrating a configuration of an assist system according to the sixteenth embodiment.

FIG. 23 is a diagram showing a configuration of an assist system 14N according to the sixteenth embodiment. Specifically, FIG. 23 is a view corresponding to FIG. 5. The assist system 14N shown in FIG. 23 is similar to the assist system 14L described in the fourteenth embodiment, except that in the assist system 14N shown in FIG. 23 the position of the first magnet 141L is changed with respect to the assist system 14L described in the fourteenth embodiment. Hereinafter, for convenience of description, the first magnet according to the sixteenth embodiment will be referred to as a first magnet 141N.

As shown in FIG. 23, the first magnet 141N is attached to the handle main body 62 at an inclined orientation relative to the line L1. Both when the operation unit 72 is closest to the handle main body 62 and when the operation unit 72 is farthest from the handle main body 62, the surface of the first magnet 141N facing the second magnet 142L (a surface on the −Z-axis side of the first magnet 141N) faces the same surface of the second magnet 142L (+Z-axis side of the second magnet 142L). However, in the different positions of the operation unit 72 (relative to the handle main body 62), the surface of the first magnet 141N facing the second magnet 142L is at a different orientation relative to the surface of the second magnet 142L.

According to the sixteenth embodiment described above, in addition to the effects similar to those of the fourteenth embodiment described above, the following effects can be obtained. The treatment instrument 2 according to the sixteenth embodiment includes the above-described assist system 14N. Therefore, when the operation unit 72 is close to the handle body 62, it is possible to increase the magnetic force due to the assist system 14L in an accelerated manner.

In an alternative embodiment of the assist system 14N according to the sixteenth embodiment described above, the first magnet 141N may be attached to the operation unit 72 side and the second magnet 142L may be attached to the handle main body 62 side. At this time, the first magnet 141N and the second magnet 142L are in a state that is inverted with respect to the YZ plane (and with respect to the state shown in FIG. 23).

Seventeenth Embodiment

Next, a seventeenth embodiment will be described. In the following description, the same reference numerals will be used for the same configurations as in the fifteenth embodiment described above, and detailed description thereof will be omitted or simplified. In the treatment instrument 2 according to the seventeenth implementation, the arrangement of the assist system is changed with respect to the assist system 14M described in the fifteenth embodiment. Hereinafter, for convenience of explanation, the assist system according to the seventeenth embodiment will be described as an assist system 14O.

Figure 24:
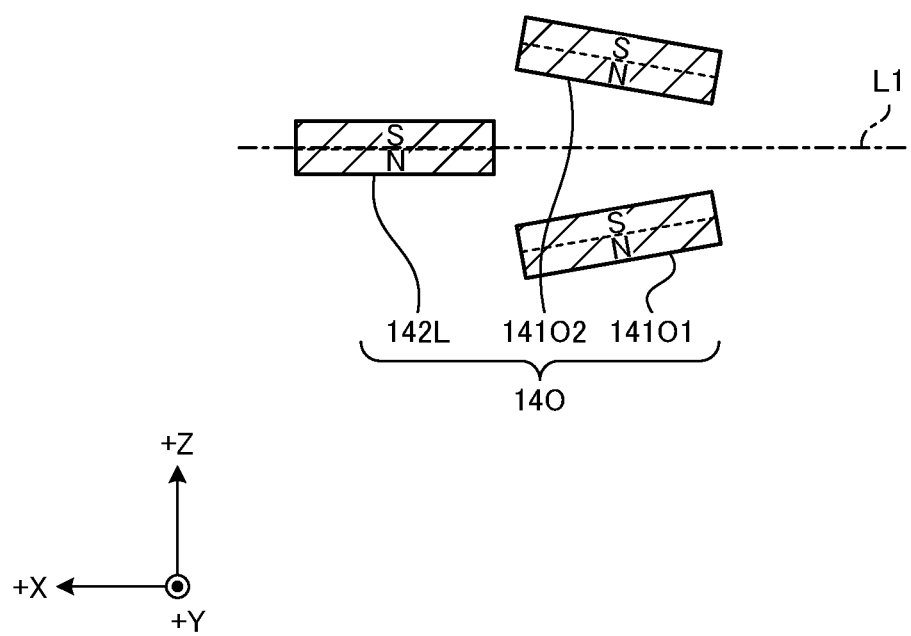
FIG. 24 is a diagram illustrating a configuration of an assist system according to the seventeenth embodiment.

FIG. 24 is a diagram illustrating a configuration of an assist system 14O according to the seventeenth embodiment. Specifically, FIG. 24 is a view corresponding to FIG. 5. The assist system 14O shown in FIG. 24 is similar to the assist system 14M described in the fifteenth embodiment, except that in the assist system 14O shown in FIG. 24 the position of the pair of first magnet 141M1,141M2 is changed. Hereinafter, for convenience of explanation, the first magnet according to the seventeenth embodiment will be described as a first magnet 141O1,141O2, which form a pair.

As shown in FIG. 24, each magnet in the pair of first magnets 141O1,141O2, is attached to the handle main body 62 at an inclined orientation relative to the line L1.

Both when the operation unit 72 is closest to the handle main body 62 and when the operation unit 72 is farthest from the handle main body 62, the surfaces of each of the first magnets 141O1,141O2 facing the second magnet 142L (a surface on the +Z-axis side of first magnet 141O1 and a surface on the −Z-axis side of first magnet 141O2) faces a respective surface of the second magnet 142L. In the case of the surface on the +Z-axis side of first magnet 141O1, it faces the −Z-axis side of the second magnet 142L and in the case of the surface on the −Z-axis side of first magnet 141O2, it faces the +Z-axis side of the second magnet 142L.

Further, in the different positions of the operation unit 72 (relative to the handle main body 62), the noted surfaces of each of the first magnets 141O1,141O2 facing the second magnet 142L is at a different orientation relative to the noted surface of the second magnet 142L. For example, in the different positions of the operation unit 72 (relative to the handle main body 62), the surface on the +Z-axis side of first magnet 141O1 facing the −Z-axis side of the second magnet 142L is at a different orientation relative to the surface of the −Z-axis side second magnet 142L and, similarly, the surface on the −Z-axis side of first magnet 141O2 facing the +Z-axis side of the second magnet 142L is at a different orientation relative to the surface of the +Z-axis side second magnet 142L.

Even when the assist system 14O according to the seventeenth embodiment described above is employed, the same effect as in the sixteenth embodiment described above is achieved.

In an alternative embodiment of the assist system 14O according to the seventeenth embodiment, the pair of first magnets 141O1,141O2 may be attached to the operation unit 72 side and the second magnets 142L may be attached to the steering wheel main body 62 side. At this time, the first magnet 141O1,141O2 and the second magnet 142L are inverted with respect to the YZ plane (and with respect to the state shown in FIG. 24).

Other Embodiments

While embodiments for carrying out the present invention have been described above, the present invention is not to be limited only by the above-described first to seventeenth embodiments.

In the first to seventeenth embodiments described above, the biasing member (the first and second biasing members 15 and 16) according to the present invention is not limited to a coil spring, and other biasing members, such as a micro-mechanical system, may be employed.

In the first to seventeenth embodiments described above, a configuration in which a jaw 12 (which is a second grip piece according to the present invention) opens and closes with respect to a vibration transmission member 13 (which is a first grip piece according to the present invention) has been employed, but the present invention is not limited thereto. For example, both the first and second gripping pieces may employ a configuration in which both the first and second gripping pieces are opened and closed by moving.

In the first to seventeenth embodiments described above, the treatment instrument according to the present invention is configured to impart both ultrasonic energy and high frequency energy to a target site, but the present invention is not limited thereto, and may be configured to impart at least one of ultrasonic energy, high frequency energy, and thermal energy. Here, "imparting heat energy to a target site" means transmitting heat generated in a heater or the like to a target site.

DESCRIPTION OF SYMBOLS

1 Treatment system
2 Treatment instrument
3 Controller
4 Handpiece
5 Ultrasonic transducer
6 Fixed handle
7 Movable handle
8 Switch
9 Rotary knob
10 Shaft
11 opening and closing mechanism
12 Jaw
13 Vibration transmission member
14, 14A-14O assist system
15 First biasing member
16 Second biasing member
51 Transducer (TD) case
52 Ultrasonic transducer
61 Case body
62 Handle body
71 Handle base
72 Operating unit
73 Connecting portion
101 First pin
102 Notch
111 Inner pipe
112 Holding portion
113 Slider receiver
114 Slider
121 Second pin
131 Treatment portion
141, 141E,141G,141L,141M1,141M2,141N,141O1, 141O2 first magnets
142, 142D,142F,142L second magnets
142A ferromagnet
143-146 Impact alleviation member
521 Front mass
711 Engagement portion
1111 Arm portion
1411,1413 Base portion
1412,1414 Convex portion
1421,1423 Base portion
1422,1424 Convex portion
Ar1 distal end side
Ar2 proximal end side
Ax central axis
C Electrical cable
L1 Line representing the movement of a locus of the magent(s)
Rx1 first rotational shaft
Rx2 second rotational shaft
TO Outer tube
TI inner tube

What is claimed is:

1. A treatment instrument, comprising:
a first gripping piece;
a second gripping piece configured to open and close with respect to the first gripping piece;
a shaft connected to the second gripping piece at a distal end of the shaft;
a fixed handle configured to connect to a proximal end of the shaft;
a movable handle configured to move in a direction close to or away from the fixed handle;
a biasing member having a biasing force and configured to bias the movable handle in a direction away from the fixed handle; and
an assist member having an attracting force and configured to attracting the movable handle with respect to the fixed handle,
wherein the second gripping piece is configured to approach with respect to the first gripping piece by moving in a direction toward the first gripping piece in response to a first user operation to the movable handle, wherein the second gripping piece is configured to move away from the first gripping piece by moving in a direction away from the first gripping piece in response to a second user operation to the movable handle, wherein a moving range of the movable handle includes a first range and a second range, wherein the first range is from a first state of the movable handle to a second state of the movable handle, wherein in the first state the second gripping piece is most away from the first gripping piece and in the second state the second gripping piece is most close to the first gripping piece while at the same time the first gripping piece and the second gripping piece are not in contact, wherein the second range is from the second state of the movable handle to a third state of the movable handle, wherein in the third state the first gripping piece and the second gripping piece are in contact piece, and wherein, in the second range, the attracting force is smaller than the biasing force.

2. The treatment instrument according to claim 1, wherein movement of the movable handle in the moving range is opposed by a friction force, and wherein, in the second range, the attracting force is smaller than a sum of the attracting force and the friction force.

3. The treatment instrument according to claim 2, wherein a difference between the sum of the biasing force and the friction force and the attracting force defines a gripping force, and wherein the gripping force is smallest in the second range.

4. The treatment instrument according to claim 3, wherein the gripping force is smallest at a position of the movable handle when the movable handle is closest to the fixed handle force defines a gripping force.

5. The treatment instrument according to claim 1, wherein the attracting force in the first range is 30 percent or less of the attracting force in the second range.

6. The treatment instrument according to claim 1, wherein the biasing member includes a first biasing member; and wherein the first biasing member is configured to bias the movable handle in the direction away from the fixed handle only when the movable handle is in the second range.

7. The treatment instrument according to claim 6, wherein the biasing member includes a second biasing member, and wherein the second biasing member is configured to bias the movable handle in the direction away from the fixed handle when the movable handle is in both the first range and the second range.

8. The treatment instrument according to claim 1, wherein the assist member includes a magnet, and wherein the magnet is provided on at least one of the fixed handle and the movable handle.

9. The treatment instrument according to claim 1, wherein the assist member includes a magnet and a ferromagnetic body, wherein the magnet is provided on at least one of the fixing handle and the movable handle, and wherein the ferromagnetic body is provided on the other of the fixed handle and the movable handle.

10. The treatment instrument according to claim 1, wherein the assist member includes an impact relieving member that mitigates impact when the movable handle is in closest proximity to the fixed handle.

11. The treatment instrument according to claim 10, wherein the impact relieving member is composed of an elastomeric material or an elastomeric body.

12. The treatment instrument according to claim 1, wherein the treatment instrument is configured to apply ultrasonic energy to a biological tissue.

13. The treatment instrument according to claim 1, wherein the assist member includes a magnet provided on at least one of the fixed handle and the movable handle, and wherein the magnet has a convex portion protruding toward the other of the fixed handle and the movable handle.

14. The treatment instrument according to claim 13, wherein the assist member includes an impact relieving member that mitigates impact when the movable handle is in closest proximity to the fixed handle.

15. The treatment instrument according to claim 1, wherein the assist member includes a first magnet provided on the fixed handle and a second magnet provided on the movable handle, wherein the first magnet and the second magnet are opposed to each other in a direction along a line that traces a movement locus of the second magnet moving with the movable handle in a state where the movable handle is closest to the fixed handle, and wherein magnetizing directions of the first magnet and the second magnet are along the line.

16. The treatment instrument according to claim 1, wherein the assist member includes a first magnet provided on the fixed handle and a second magnet provided on the movable handle, wherein the first magnet and the second magnet are opposed to each other in a direction perpendicular to a line that traces a movement locus of the movable handle with respect to the fixed handle in a state where the movable handle is closest to the fixed handle, and wherein magnetizing directions of the first magnet and the second magnet each intersect the line.

17. The treatment instrument according to claim 16, wherein magnetizing directions of each of the first magnet and the second magnet are perpendicular to the line.

18. The treatment instrument according to claim 16, wherein one of the first magnet and the second magnet has a surface that is opposed to the other of the first magnet and the second magnet in a state where the movable handle is closest to the fixed handle, and wherein the first magnet and the second magnet are arranged such that the surface is inclined to and faces a side of the other of the first magnet and the second in a state where the movable handle is most away from the fixed handle.

19. The treatment instrument according to claim 1, wherein the biasing member includes a coil spring or a micro-mechanical system, and wherein the assist member includes a magnet.

20. The treatment instrument according to claim 1, wherein the treatment instrument is a medical treatment instrument for conducting a procedure that imparts treatment energy to a target site to be treated in a biological tissue, and wherein the second gripping piece configured to open and close with respect to the first gripping piece is configured to grasp the target site between the first gripping piece and the second gripping piece during the procedure.

* * * * *